United States Patent
Noda et al.

(10) Patent No.: US 7,182,916 B2
(45) Date of Patent: Feb. 27, 2007

(54) METHOD AND THE DEVICE FOR MICRO-PARTICLE ARRAY FABRICATION

(75) Inventors: Hideyuki Noda, Kokubunji (JP); Yoshinobu Kohara, Kokubunji (JP); Kazunori Okano, Shiki (JP)

(73) Assignee: Hitachi, Ltd., Tokyo (JP)

( * ) Notice: Subject to any disclaimer, the term of this patent is extended or adjusted under 35 U.S.C. 154(b) by 575 days.

(21) Appl. No.: 10/321,589

(22) Filed: Dec. 18, 2002

(65) Prior Publication Data
US 2003/0198575 A1  Oct. 23, 2003

(30) Foreign Application Priority Data
Apr. 19, 2002  (JP)  ............................. 2002-117487

(51) Int. Cl.
*B01L 3/02*  (2006.01)
(52) U.S. Cl. .......................... 422/100; 422/63; 422/65; 422/99; 422/104; 436/54; 436/180
(58) Field of Classification Search ................ 422/100, 422/63, 65, 99, 104; 436/54, 180
See application file for complete search history.

(56) References Cited
U.S. PATENT DOCUMENTS
5,935,859 A * 8/1999 Elliott et al. .................. 436/54

FOREIGN PATENT DOCUMENTS
JP  11-243997  3/1998
JP  2000-346842  4/2000

OTHER PUBLICATIONS
Stephen P. A. Fodor, J. Leighton Read, Michael C. Pirrung, Lubert Stryer, Amy Tsai Lu, Dennis Solas, "Light-Directed, Spatially Addressable Parallel Chemical Synthesis", Science, vol. 251 (Feb. 15, 1991)), pp. 767-773.

(Continued)

Primary Examiner—Jill Warden
Assistant Examiner—Jyoti Nagpaul
(74) Attorney, Agent, or Firm—Reed Smith LLP; Stanley P. Fisher, Esq.; Juan Carlos A. Marquez, Esq.

(57) ABSTRACT

There are provided a novel method and technology for arraying micro-particles. Micro-particle trapping capillaries each having an inner diameter smaller than the outer diameter of probe-immobilized micro-particles are prepared. By vacuuming the inside of each micro-particle trapping capillary, only one of the micro-particles is vacuumed onto an opening at the tip thereof and taken out from holders holding a plurality of the micro-particles. The micro-particle vacuumed onto the opening at the tip of each micro-particle trapping capillary is positioned at the opening of the capillary or the edge of each channel provided in a chip, the channels each having an inlet and an outlet with a slightly larger width than the outer diameter of the micro-particle so as to allow passage of only one micro-particle. The micro-particle vacuumed onto the opening at the capillary tip is injected into the capillary from the opening of the capillary or the channel edge of the chip.

11 Claims, 14 Drawing Sheets

OTHER PUBLICATIONS

Anthony V. Lemmo, Jeffrey T. Fisher, H. Mario Geysen and Donald J. Rose, "Characterization of an Inkjet Chemical Microdispenser for Combinatorial Library Synthesis", Analytical Chemistry, vol. 69, No. 4, Feb. 15, 1997, pp. 543-551.

Tadashi Okamoto, Tomohiro Suzuki and Nobuko Yamamoto, "Microarray Fabrication with Covalent Attachment of DNA Using Bubble Jet Technology", Nature Biotechnology, vol. 18, Apr. 2000, pp. 438-441.

R. Jerrold Fulton, Ralph L. McDade, Perry L. Smith, Laura J. Kienker and John R. Kettman, Jr., "Advanced Multiplexed Analysis with the FlowMetrix™ System", Clinical Chemistry, vol. 43, No. 9 (1997), pp. 1749-1756.

Yoshinobu Kohara, Hideyuki Noda, Kazunori Okano and Hideki Kambara, "DNA Hybridization Using 'Bead-Array': Probe-Attached Beads Arrayed in a Capillary in a Predetermined Order", Nucleic Acids Research Supplement No. 1, pp. 83-84.

* cited by examiner

METHOD AND THE DEVICE FOR MICRO-PARTICLE ARRAY FABRICATION

FIELD OF THE INVENTION

The present invention relates to method and apparatus for arraying micro-particles in a capillary or a chip provided with channels therein. More particularly, it relates to method and apparatus for arraying micro-particles each having probes of biomaterials such as DNAs, RNAs, or proteins immobilized thereon in a given order, and thereby enabling the examinations of various test items at a time.

BACKGROUND OF THE INVENTION

With the advance of the Human Genome Program, a strong movement has been under way to understand living bodies on the DNA level, and thereby to understand the tests of diseases and life phenomena. Investigation on the expression profiles of genes is effective for understanding life phenomena and investigating the actions of genes. As an effective method for investigating the gene expression profile, a DNA probe array obtained by immobilizing a large number of DNA probes in groups divided according to the kinds thereof on the surface of a solid such as slide glass, or a DNA chip, or further a protein chip has come into use.

Examples of a technology for fabricating such a chip include: a method in which an oligomer with a designed sequence is synthesized base by base in each of a large number of cells sectioned on a slide glass by using a lithography technology to be widely used in a photochemical reaction and the semiconductor industry (Science 251, 767–773 (1991); and a method in which a plurality of kinds of DNA probes are spotted one by one to each segment (Anal. Chem. 69, 543–551 (1997), Nat. Biotechnol., 18, 438–441 (2000)).

On the other hand, another method is proposed, wherein micro-particles having DNA probes immobilized thereto are prepared, and a plurality of kinds of such micro-particles are collected, thereby to fabricate a probe array (Clinical Chemistry 43, 1749–1756 (1997), Nucleic Acids Research Supplement No. 1, 83–84 (2001)). Use of micro-particles has an advantage in that a probe array having no variation in probe density between micro-particles can be fabricated because a probe immobilizing method utilizing chemical reactions in a solution is usable.

For the probe array on a slide glass, the following method is adopted. Namely, the probe species is identified according to the oligomer formation position or the spot position of each DNA probe or protein probe. As for the probe array using probe conjugated micro-particles, there is adopted a method in which micro-particles color coded for respective probes are used (Clinical Chemistry 43, 1749–1756 (1997)), or a method in which the probe species is identified according to the arraying order of the micro-particles in a capillary (Nucleic Acids Research Supplement No. 1, 83–84 (2001)).

In the prior art, any method of fabrication of a DNA probe array or a DNA chip requires the immobilization of DNA probes or synthesis of oligomers base by base for every array. Therefore, the fabrication requires much time and trouble, resulting in a high fabrication cost. Further, the probes are immobilized each in droplet form on the solid surface. This presents the following deficiencies: for example, the probes vary from one section to another section; the combination of probe species is not easy to change; and a user cannot operate them with ease.

In order to solve the foregoing problems, there was proposed a probe array using micro-particles, i.e., micro-particle array, obtained by separate steps of immobilizing probes on the solid surfaces and arraying the probes (Nucleic Acids Research Supplement No. 1, 83–84 (2001)). In order to achieve practical utilization of the micro-particle array, and to sell the micro-particle array positioned in a capillary or a chip at a low price, it is essential to establish apparatus and method for selecting given probe-immobilized micro-particles according to the test purpose, and arraying the micro-particles as desired.

Heretofore, as this technology, the following methods have been proposed: a method in which micro-particles are poured into a capillary utilizing the flow of a liquid on a one-by-one basis under control (Japanese Laid-Open Patent Publication No. Hei 11-243997); and a method in which only one micro-particle out of a plurality of micro-particles introduced together with a solvent is held on a sheet provided with a micro-hole capable of receiving only one micro-particle, and the sheet holding the micro-particle is moved to a position of a capillary or a channel provided in a flat plate for arrangement (Japanese Laid-Open Patent Publication No. 2000-346842) However, with these methods, the micro-particles may not be efficiently captured under the influence of bubbles, resulting in inferior reliability and operability.

Thus, the apparatus for arraying micro-particles as desired, and a method thereof are yet to be established. It is therefore an object of the present invention to provide novel method and technology for establishment thereof.

SUMMARY OF THE INVENTION

In order to solve the foregoing problems, in the present invention, it has become possible to fabricate a micro-particle array with ease and reliability in the following manner. (1) Micro-particle trapping capillaries each having an inner diameter smaller than the outer diameter of each of probe-immobilized micro-particles to be used are prepared. (2) By vacuuming of the inside of each of the micro-particle trapping capillaries, only one of the micro-particles is vacuumed onto an opening at the tip thereof and taken out from holders holding a plurality of the micro-particles therein. (3) The micro-particle vacuumed onto the opening at the tip of each micro-particle trapping capillary is positioned at the opening of a capillary of micro-particle array for arraying the micro-particles or the edge of each of channels provided in a chip, the channels each having an inlet and an outlet with a slightly larger width than the outer diameter of the micro-particle so as to allow passage of only one of the micro-particles therethrough. (4) The micro-particle vacuumed onto the opening at the micro-particle trapping capillary tip is injected into the capillary of micro-particle array from the opening of the capillary of micro-particle array or the channel edge of the chip.

Figure 1:
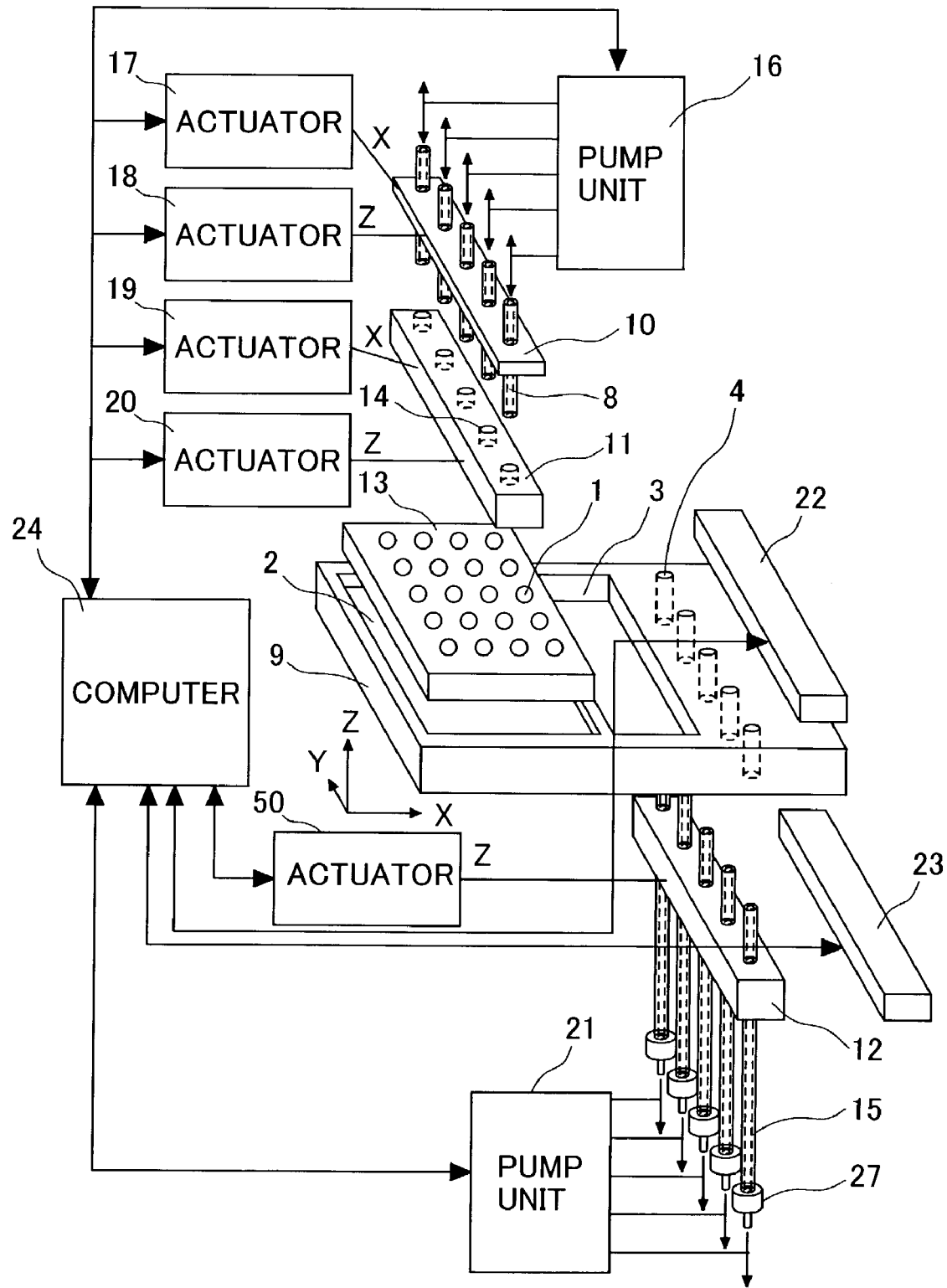
FIG. 1 is a diagram for schematically showing the configuration of a device for micro-particle array fabrication of a first example of the present invention.

DETAILED DESCRIPTION OF THE
PREFERRED EMBODIMENTS

First, a micro-particle holding plate having m×n holders, a group of micro-particles, and a plurality of kinds of DNA, RNA, or protein probes modifying the micro-particles are prepared. A large number of the micro-particles with roughly the same outer diameter are prepared. The micro-particles are preferably spherical ones with a size in outer diameter of about 30 to 100 μm. However, by optimizing the pressure of vacuuming or pressurization through the opening at the tip of the capillary, and the outer diameter and the inner diameter of the micro-particle trapping capillary, it is also possible to use micro-particles having an outer diameter in the range of 5 μm to 10 mm.

The prepared micro-particles are distributed in units of several milligrams to respective holders of the micro-particle holding plate by using a spatula. A different kind of probe is introduced to each row of the holders, or to each holder of the micro-particle holding plate, so that the probes are immobilized on the surfaces of all the micro-particles in the holders of the micro-particle holding plate. As a result, it is possible to prepare the micro-particle holding plate holding a plurality of kinds of probe-immobilized micro-particle groups, of which the kinds of the probes are distinguishable according to the positions of their respective holders, and this is placed at a prescribed position.

On the other hand, there is prepared a capillary for forming a micro-particle array, having an inner diameter slightly larger than the outer diameter of the micro-particle so as to allow passage of only one of the micro-particles therethrough, or a chip provided with channels each having an inlet and an outlet with a width slightly larger than the outer diameter of the micro-particle so as to allow passage of only one of the micro-particles therethrough. The capillary or the chip is disposed at a prescribed site at a different position from that of the micro-particle holding plate. Herein, desirably, the capillaries for forming a micro-particle array or the channels of the chip are prepared in a number corresponding to the number m or n of the holders per row of the micro-particle holding plate to be used, and disposed in a single row at the same spacing as that between the holders of the micro-particle holding plate. Further, micro-particles having probes immobilized on their surfaces are supplied from the opening ends of the capillaries for forming a micro-particle array or one ends of the channels of the chip. For this reason, each of the other ends thereof is connected to a pump via a port smaller than the outer diameter of the micro-particle, impassable for the micro-particle for vacuuming.

There are prepared a pump capable of vacuuming and pressurizing, and a tube of which one end is connected to the pump, and thereby which is capable of arbitrarily selecting vacuuming or pressurizing by switching of a valve. To the other end of the tube, is attached each micro-particle trapping capillary. The inner diameter of the micro-particle trapping capillary is set to be smaller than the outer diameter of the micro-particle. This allows one micro-particle to be vacuumed on the tip opening of the micro-particle trapping capillary, but prevents it from passing through the capillary. Herein, desirably, the micro-particle trapping capillaries are prepared in a number corresponding to the number m or n of the holders per row of the micro-particle holding plate to be used, and disposed in a single row at the same spacing as that between the holders of the micro-particle holding plate. Further, the open ends of the micro-particle trapping capillaries, i.e., the tips of the micro-particle trapping capillaries, which are for trapping the micro-particles and disposed in a row, are all aligned at the same height.

The micro-particle holding plate which holds a plurality of kinds of probe-immobilized micro-particle groups and the capillaries for forming a micro-particle array or the channels in the chip are disposed at their respective prescribed positions. Under such a state, the tip of each micro-particle trapping capillary is introduced into the holder holding the desired probe-immobilized micro-particle group therein. The tube is then rendered in a vacuuming state, so that the micro-particle is vacuumed onto the opening at the tip of each micro-particle trapping capillary. Thereafter, the tip of the micro-particle trapping capillary, vacuuming the micro-particle onto its opening at the tip is moved to the opening of the capillary for forming a micro-particle array or to one end of each channel of the chip, so that both are positioned in opposed relation to each other. The tube is switched to the pressurizing state, so that the micro-particle vacuumed onto the tip of the micro-particle trapping capillary is moved to the open end of the capillary for forming a micro-particle array or to one end of each channel of the chip. The other end of the capillary for forming a micro-particle array or the channel of the chip is connected to a pump via a port smaller than the outer diameter of the micro-particle and impassable for the micro-particle, for vacuuming. Accordingly, a desired probe-immobilized micro-particle is introduced into the capillary for forming a micro-particle array or the channel of the chip.

By repeating such operations while replacing the micro-particle with another micro-particle, it is possible to fabricate a micro-particle array or chip having a row of micro-particles with probes of desired sequences immobilized thereto. In order that this procedure can be performed on a row-by-row basis of the micro-particle holding plate, a plurality of capillaries or the channels of the chip for forming a micro-particle array, and the micro-particle trapping capillaries are arranged in a number equal to the number of the rows of the micro-particle holding plate. As a result, it is possible to enhance the working efficiency.

Incidentally, when the micro-particle is vacuumed onto the opening at the tip of the micro-particle trapping capillary in the holder of the micro-particle holding plate, it is not that only one micro-particle is ideally vacuumed onto the tip of the micro-particle trapping capillary, but that a plurality of micro-particles may be attached to the perimeter of the tip of the capillary. Therefore, it is advantageous to enable the situation where only one micro-particle is vacuumed onto the micro-particle trapping capillary tip in process of performing the foregoing operation. For this reason, for example, it is advantageous to dispose an adherent micro-particle removing plate capable of removing excess adherent micro-particles above the micro-particle holding plate. The adherent micro-particle removing plate is so configured as to have through holes each with a larger inner diameter than the outer diameter of the micro-particle trapping capillary. Further, the inner diameter of the through hole is set to a dimension allowing the passage of the micro-particle vacuumed onto the opening at the tip of the micro-particle trapping capillary together with the micro-particle trapping capillary therethrough. In consequence, when the micro-particle trapping capillary is pulled up together with the adherent micro-particle through the through hole of the adherent micro-particle removing plate after the micro-particle trapping capillary has vacuumed the micro-particle thereon, it is possible to forcedly scrape off a plurality of micro-particles adhering to the perimeter of the tip of the micro-particle trapping capillary. In this case, it is not possible to directly scrape off the micro-particle adhering to the tip of the micro-particle vacuumed onto the opening of the trapping capillary by contact with the sidewall of the through hole of the adherent micro-particle removing plate. However, since the adhesion of each of such adherent micro-particles is weak, the adherent micro-particles will separate therefrom, pulled by their respective surrounding adherent micro-particles being scraped off. Further, in order to remove the second and more micro-particles with more reliability, desirably, the adherent micro-particle removing plate is sifted sideways together with the tip of the micro-particle trapping capillary above the plane of the micro-particle holding plate. As a result, the second and more micro-particles are scraped off at the interface between the micro-particle holding plate and the adherent micro-particle removing plate. When a plurality of micro-particle trapping capillaries are disposed, the through holes of the adherent micro-particle removing plate are desirably disposed in a row and in a number corresponding thereto.

When the micro-particles are held together with a solvent such as pure water in the holder of the micro-particle holding plate, a plurality of unnecessary micro-particles will be scraped off at the interface between air and the solvent by using the micro-particle trapping capillary having an outer diameter about 1.5 times the outer diameter of the micro-particle to be used. Therefore, in such a case, the adherent micro-particle removing plate is not required.

Herein, it is desirable for an electrically operated manipulator controlled by a so-called sequential control programmed personal computer to perform the following operations: the movement of the micro-particle trapping capillary into the holder of the micro-particle holding plate; the vacuuming of the micro-particle onto the opening at the tip of the micro-particle trapping capillary; and the movement of the micro-particle trapping capillary which has vacuumed the micro-particle thereon to the capillary for forming a micro-particle array or the channel of the chip. Further, the vacuuming and pressurizing operations in accordance with these operations are also desirably accomplished through a program operation by the personal computer.

Thus, in accordance with the present invention, by arraying the micro-particles one by one in each capillary for forming a micro-particle array or each channel of the chip, it is possible to fabricate a micro-particle array (a vessel for forming a micro-particle group) targeted for DNAs, RNAs, and proteins surely with efficiency at a low cost. Further, the device in accordance with the present invention is also applicable to the fabrication of a planar micro-particle array.

Below, the present invention will be described in details by way of examples with reference to the accompanying drawings. In the following description, the outer diameter of a micro-particle to be used is set to be 0.1 mm for simplification.

FIRST EXAMPLE

FIG. 1 is a diagram for schematically showing the device configuration of a device for micro-particle array fabrication of First Example of the present invention. A reference numeral 9 denotes a base, and it is composed of a plate member. Herein, for convenience of description below, x-, y-, and z-axes are defined as shown in the diagram based on the configuration of the base 9. When the movement direction, the relative positional relationship, and the like are required to be described, they will be described based on the axes.

The base 9 is provided with a plate mounting site 2, a washing vessel 3, a plurality of movement assist through holes 4, and a first vision sensor 22 and a second vision sensor 23.

The plate mounting site 2 is formed in the shape of a shallow vessel. A micro-particle holding plate 13 is positioned in such a manner as to be inserted in the vessel. The micro-particle holding plate 13 has a total of m×n holders, m holders along the x axis (row), and n holders along the y axis (line) Each holder of the micro-particle holding plate 13 holds micro-particles having probes, which will bind to a biomaterial serving as a target to be tested, immobilized thereto. Incidentally, in FIG. 1, for simplification, it is set that m=4 and that n=5. However, in an actual configuration example, for example, a microplate including holders 1 each having a 3.5-mm-dia circular upper opening and a depth of 9.6 mm can be disposed, and the one having a total of 384 holders, 24 holders along the x axis (m=24) and 16 holders along the y axis (n=16) can be used.

In the washing vessel 3, the tip portion of each micro-particle trapping capillary 8 and an adherent micro-particle removing plate 11 are immersed after the micro-particle trapping capillary 8 has trapped a micro-particle, and the micro-particle has been transferred onto a micro-particle array forming capillary, and before the process shifts to the operation of trapping the next micro-particle. The washing vessel 3 is charged with a washing solution suitable for preventing contamination, and applied with an ultrasonic vibration for enhancing the washing effect.

The n movement assist through holes 4 are disposed in parallel with the holders arranged along the y axis of the micro-particle holding plate 13, and at the same spacing as that between the holders. The movement assist through hole 4 is circular in cross section, and has a central axis parallel to the z axis. The movement assist through holes 4 guide a group of a plurality of the micro-particle trapping capillaries and a group of a plurality of capillaries of micro-particle array as described later. Thus, each of the holes 4 assists the transfer of the micro-particle vacuumed onto the opening at the tip of the micro-particle trapping capillary to the capillary of micro-particle array. Therefore, it has such an inner diameter as to allow the capillary to move with safety. For example, it has a diameter of 0.4 mm when the micro-particle trapping capillary has an outer diameter of 0.15 mm, and an inner diameter of 0.05 mm.

The first vision sensor 22 is disposed at a position parallel to and adjacent to the movement assist through holes 4. The vision sensor 22 is used for checking whether or not the micro-particle is being trapped onto the opening at the tip of each micro-particle trapping capillary 8 prior to the introduction of the micro-particle trapping capillary 8 into the movement assist through hole 4. When the output from the first vision sensor 22 indicates that there is the opening at the tip of the micro-particle trapping capillary 8 onto which no micro-particle is trapped, the process goes back to the operation of trapping the micro-particle by the micro-particle trapping capillary 8.

The second vision sensor 23 is disposed at a position opposing to the first vision sensor 22, and on the bottom side of the base 9. It is used for checking whether or not the micro-particle has been introduced into the capillary of micro-particle array 15. When the output from the second vision sensor 23 indicates that the micro-particle has not been introduced in the capillary of micro-particle array 15, the data instructing that the capillary of micro-particle array 15 is a defective is recorded and displayed in a computer.

The n micro-particle trapping capillaries 8 are disposed in parallel with the y axis, and at the same spacing as that between the holders 1 of the micro-particle holding plate 13. In the example of this diagram, five capillaries 8 are disposed. Whereas, in the foregoing example of the microplate, sixteen capillaries 8 are disposed in parallel with the y axis. The positions of the tip portions of the micro-particle trapping capillaries 8 are aligned with respect to the z axis, and fixedly held by a first holder 10 so as to be handled as a group. Herein, the one end of each micro-particle trapping capillary 8 is formed as an opening, and used for being inserted into the holder 1, and vacuuming a micro-particle on the opening. Further, the one end of the micro-particle trapping capillary 8 is inserted into the holder 1 via the adherent micro-particle removing plate 11. Therefore, the first holder 10 is disposed at a position away from the edge of each micro-particle trapping capillary 8 by the distance required therefor. The other end of each micro-particle trapping capillary 8 is not shown. However, as described previously, it is connected to a tube of which one end is connected to a pump capable of vacuuming and pressurizing, and thereby which is capable of arbitrarily selecting vacuuming or pressurizing by switching of a valve.

In order that the micro-particle trapping capillary 8 can vacuum and trap only one micro-particle onto the opening at its tip, it suffices that the relationship expressed as ID<<R is satisfied, where ID denotes the inner diameter of the micro-particle trapping capillary 8, and R denotes the outer diameter of the micro-particle. In other words, it suffices that the micro-particle trapping capillary 8 have an inner diameter satisfying the relationship expressed as ID<<0.1 mm when the outer diameter of the micro-particle is 0.1 mm. Thus, the foregoing micro-particle trapping capillary 8 having an inner diameter of 0.05 mm is appropriately used.

In the example shown in FIG. 1, five micro-particle trapping capillaries 8 arrayed along the y axis are shown for simplification. However, in the configuration of the example of the microplate, for example, in the first holder 10 having dimensions of 100 mm×15 mm and a thickness of 10 mm, 16 micro-particle trapping capillaries 8 each with an inner diameter of 0.05 mm, an outer diameter of 0.15 mm, and a given length are fixed along the y axis at a spacing of 4.5 mm. The distance from the opening at the tip to the first holder 10 is set to be about 15 mm in view of the depth of the holder 1 of 9.6 mm if the thickness of an adherent micro-particle removing plate is assumed to be 5 mm.

A reference numeral 11 denotes the foregoing adherent micro-particle removing plate, which is disposed for the purpose of, when a micro-particle has been vacuumed onto the opening of the micro-particle trapping capillary 8, removing other micro-particles adhering to the tip portion thereof. In the adherent micro-particle removing plate 11, n adherent micro-particle removing holes 14 are disposed in parallel with the y axis, and at the same spacing as that between the holders 1 of the micro-particle holding plate 13, and they also correspond to the micro-particle trapping capillaries 8. In the example of the diagram, there are five holes 14. However, in the configuration of the foregoing example of the microplate, sixteen holes 14 are disposed in parallel with the y axis. The adherent micro-particle removing hole 14 is circular in cross section, and has a central axis parallel to the z axis. The inner diameter of the adherent micro-particle removing hole 14 is determined so that a plurality of micro-particles adhering to the perimeter of the tip of the micro-particle trapping capillary 8 will be forcedly scraped off when the micro-particle trapping capillary 8 is pulled up together with the adherent micro-particles after the micro-particle trapping capillary 8 has vacuumed the micro-particle thereon. Any diameter of the adherent micro-particle removing hole 14 is acceptable so long as it satisfies the following expression OD≦OD'<2R, where R denotes the outer diameter of the micro-particle, OD denotes the outer diameter of the micro-particle trapping capillary 8, and OD' denotes the diameter of the adherent micro-particle removing hole 14. For example, when the outer diameter of the micro-particle is 0.1 mm, and the outer diameter of the micro-particle trapping capillary 8 is 0.15 mm, any adherent micro-particle removing hole 14 is acceptable so long as it satisfies the expression: 0.15 mm≦OD'<0.2. Specifically, it is desirable that 0.18-mm-dia adherent micro-particle removing holes 14 are formed in a plate member having dimensions of 100 mm×15 mm and a thickness of 5 mm.

A reference numeral 15 denotes a capillary of micro-particle array. The n capillaries 15 are disposed in parallel with the y axis, and at the same spacing as that between the holders 1 of the micro-particle holding plate 13, and they also correspond to the same spacing as that between micro-particle trapping capillaries 8. In the example of the diagram, there are five capillaries 15. However, in the configuration of the foregoing example of the microplate, sixteen capillaries of micro-particle array 15 are disposed in parallel with the y axis. One end of the capillary of micro-particle array 15 is formed as an opening, and the other end thereof is connected and vacuumed to a pump via a tube. The edge of the capillary of micro-particle array 15 and the tube are desirably connected through a socket 27. Herein, the socket 27 has a smaller inner diameter than the outer diameter of the micro-particle so as to prevent the passage of the micro-particle therethrough.

In order to vacuuming micro-particles sequentially one by one into the capillary of micro-particle array 15, and arraying a plurality of the micro-particles in the inside thereof while keeping the order of being vacuumed, any inner diameter of the capillary of micro-particle array 15 is acceptable so long as it satisfies the relationship expressed as: $R<ID<2R$, where R denotes the outer diameter of the micro-particle, and ID denotes the inner diameter of the capillary of micro-particle array 15. When the outer diameter of the micro-particle is 0.1 mm, the capillary of micro-particle array 15 desirably has an inner diameter of 0.15 mm and an outer diameter of 0.38 mm.

Desirably, the edges on the opening side of the capillaries of micro-particle array 15 are fixedly held by a second holder 12 so that the positions of the tip portions of the capillaries of micro-particle array 15 are aligned with respect to the z axis, and so that they can be-handled as a group. Of course, after necessary micro-particles have been inserted therein, the capillaries of micro-particle array 15 are desirably released from holding by the second holder 12, which allows individual handling of each capillary of micro-particle array 15.

After each micro-particle trapping capillary 8 has vacuumed a micro-particle onto its tip opening, the tip opening of each micro-particle trapping capillary 8 and the opening of each capillary of micro-particle array 15 are arranged in opposed relation to each other in the movement assist through hole 4. Thus, the tube to which the micro-particle trapping capillary is connected is rendered in the pressurizing state, so that the micro-particle vacuumed onto the tip opening is released, and transferred to the capillary of micro-particle array 15.

In the foregoing actual example, the diameter of the movement assist through hole 4 is set to be 0.4 mm. Accordingly, in the foregoing example of a configuration of the microplate, the second holder 12 is so configured as to have dimensions of 100 mm×15 mm and a thickness of 10 mm. Thus, it fixes therethrough sixteen capillaries of micro-particle array 15 each with an inner diameter of 0.15 mm, an outer diameter of 0.38 mm, and a given length along the y axis at a spacing of 4.5 mm.

A reference numeral 16 denotes a vacuuming and pressurizing unit, to which one end of each micro-particle trapping capillary 8 is connected, and thereby which performs vacuuming and pressurizing for trapping and releasing the micro-particle, respectively. In actuality, the unit 16 is a system so configured that one end of each micro-particle trapping capillary 8 is connected with a tube via a socket, and coupled with a pump and an air supply system to allow arbitrary selection of vacuuming or pressurizing by switching of a valve.

A reference numeral 21 denotes a pump, to which one end of each capillary of micro-particle array 15 is connected via a tube, and thereby which is configured to be a system for performing vacuuming for trapping the micro-particle to be supplied to the opening end of each capillary of micro-particle array 15.

The socket in either case may be in any configuration so long as the capillary can be inserted and fixed therein.

The first vision sensor 22 is disposed on the top side of the base 9, and used for checking whether or not a micro-particle has been trapped on the opening at the tip of the micro-particle trapping capillary 8. In contrast, the second vision sensor 23 is disposed on the bottom side of the base 9, and used for checking whether or not the micro-particle has been introduced into the capillary of micro-particle array 15.

A reference numeral 17 denotes a first actuator, and is used for moving the first holder 10 in the direction of x axis. A reference numeral 18 denotes a second actuator, and is used for moving the first holder 10 in the direction of z axis. The position along the y axis of the first holder 10 with respect to the base 9 is assumed to be fixed. A reference numeral 19 denotes a third actuator, and is used for moving the adherent micro-particle removing plate 11 in the direction of x axis. A reference numeral 20 denotes a fourth actuator, and is used for moving the adherent micro-particle removing plate 11 in the direction of z axis. A reference numeral 50 denotes a fifth actuator, and is used for moving the second holder 12 in the direction of z axis. Each position along the y axis of the first holder 10 and the adherent micro-particle removing plate 11 with respect to the base 9 is assumed to be fixed. The positions along the x axis and the y axis of the second holder 12 with respect to the base 9 is assumed to be fixed. A reference numeral 24 denotes a computer.

The overall control including the program control of the pump and the actuators by the computer 24, and further the utilization of outputs from the vision sensors will be described below by reference to FIG. 2 and the subsequent figures.

Figure 2:
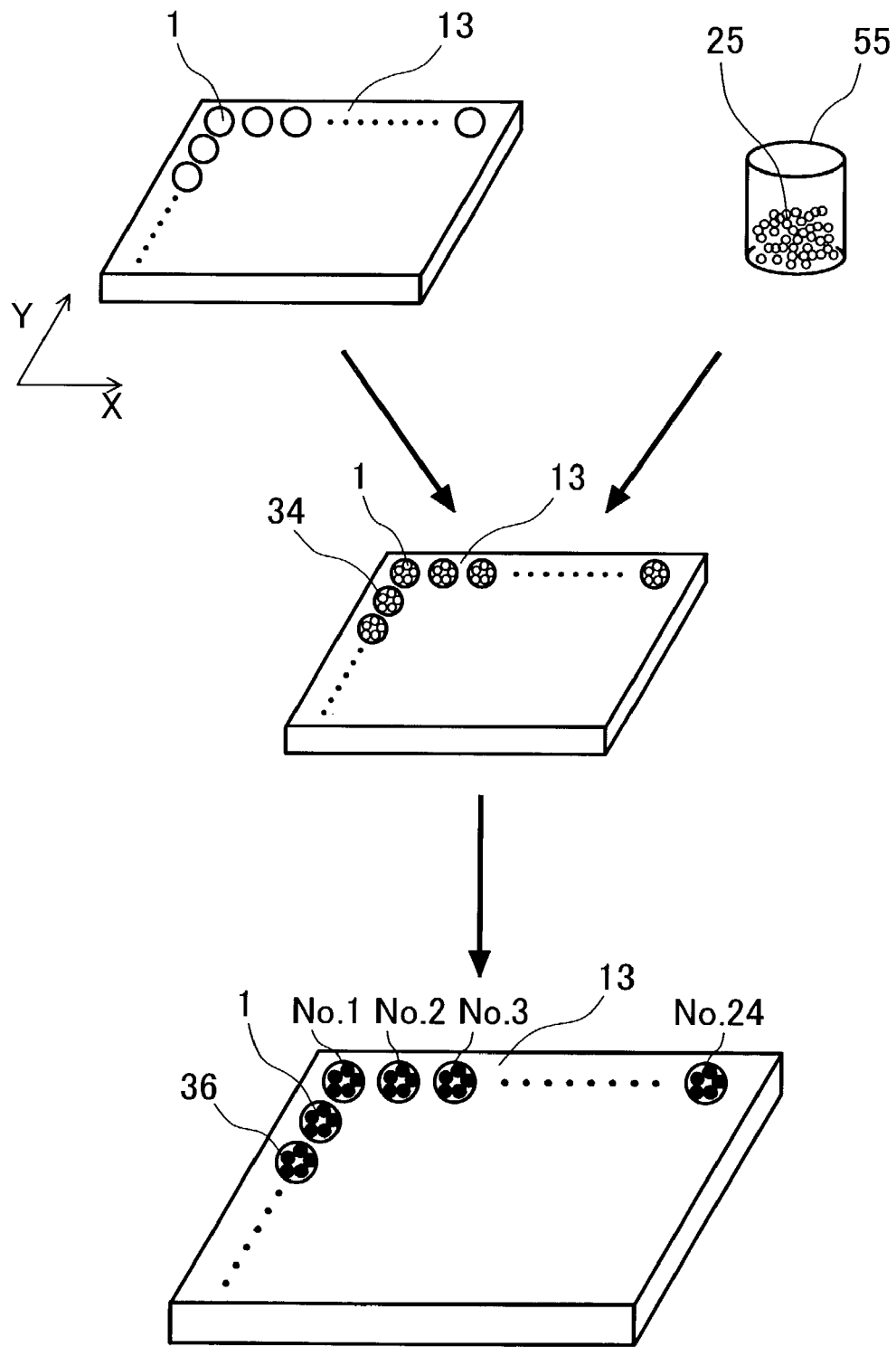
FIG. 2 is a diagram for generally illustrating a configuration example of a micro-particle holding plate 13.

FIG. 2 is a diagram for generally illustrating a configuration example of the micro-particle holding plate 13. First, the micro-particle holding plate 13 is prepared. A 384 (24×16)-hole microplate is conveniently used for this. A container 55 holding therein a plurality of micro-particles 25 are prepared. In this example, micro-particles made of glass subjected to amino-silane modification, with an outer diameter of 0.1 mm are used. Further, a plurality of the micro-particles 25 are allowed to react all at once in a 0.01% N-(4-maleimidobutyryloxy)succinimide solution (ethanol: 50%, dimethylsulfoxide: 50%) at room temperature for 1 hour in the containers 55. The resulting micro-particles are further washed in a 50% ethanol-50% dimethylsulfoxide mixed solution to prepare maleimide group induced micro-particles 34.

Then, a plurality of the maleimide group induced micro-particles 34 are distributed in units of several milligrams into respective holders 1 of the micro-particle holding plate 13 by using a spatula. Thereafter, a plurality of micro-particles 25 having the same kind of probes immobilized thereto are formed in a row of the respective holders 1 arranged along the y axis. Whereas, a plurality of micro-particles 25 having mutually different kinds of probes immobilized thereto are formed in the respective holders 1 of different rows, and along the x axis. In other words, when the 384 (24×16)-hole microplate is used, different probe-DNAs are prepared in the respective twenty-four holders 1 along the x axis, while a plurality of micro-particles 25 having the same kind of probe DNAs immobilized thereto are formed in a row of sixteen holders 1 arranged along the y axis. The immobilization of probe DNAs to the maleimide group induced micro-particles 34 is accomplished by effecting the reaction with synthetic DNAs modified with thiol group at 5' terminal, and having different base sequences. They are allowed to react in various 0.1 nM synthetic DNA—20 mM prostate-buffer (pH 7.0) at room temperature for 1 hour. Then, they are successively washed with a 20 mM phosphate buffer (pH 7.0) solution and water to obtain a plurality of DNA probe immobilized micro-particles 36. Such immobilization of the probe DNAs can be performed directly on the 384-hole microplate to which a plurality of the micro-particles 25 have been previously distributed.

Then, the operation and the control will be described. First, in the plate mounting site 2 of the base 9, the micro-particle holding plate 13 holding the micro-particles having probes immobilized thereto in their respective holders 1 is mounted. The washing vessel 3 is charged with a washing solution suitable for preventing contamination in the following manner. Namely, the tip portion of each micro-particle trapping capillary 8 and the adherent micro-particle removing plate 11 are immersed therein after the micro-particle on the tip opening of each micro-particle trapping capillary 8 has been transferred onto its corresponding capillary of micro-particle array 15, and before the process shifts to the operation of trapping the next micro-particle by the micro-particle trapping capillary 8. Further, the second holder 12 holding the capillaries of micro-particle array 15 is set in the holding portion of the fifth actuator 50.

Figure 3:
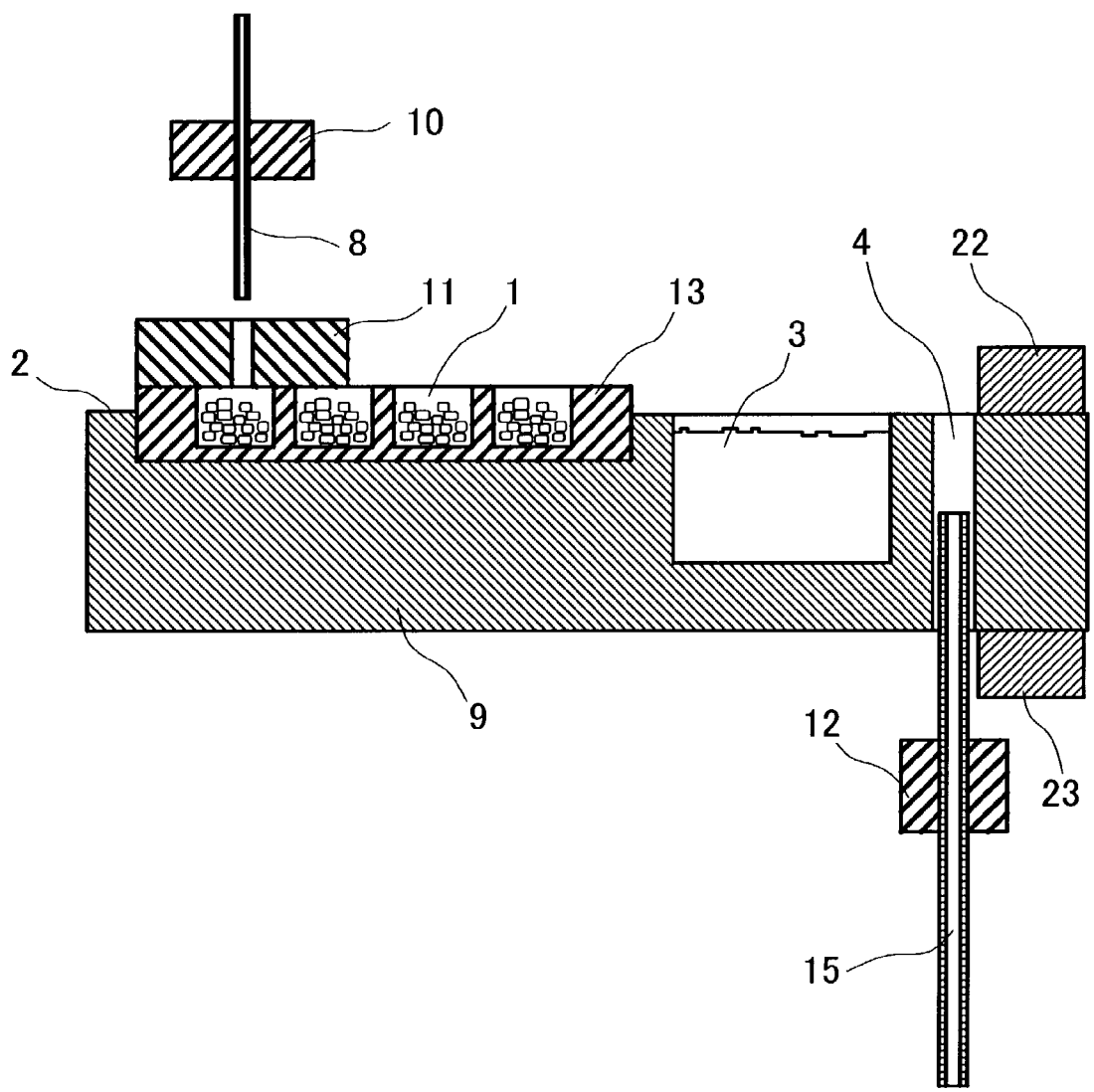
FIG. 3 is a cross sectional view along the z axis of the device for showing the state caused by execution of a preset function through a computer 24 by a user after the micro-particle holding plate 13 has been mounted, a washing vessel 3 has been charged with a washing solution, and the capillaries of micro-particle array 15 have been set.

FIG. 3 is a cross sectional view along the z axis of the device for showing, focusing attention to the central position of the base 9, the state caused by execution of a preset function through the computer 24 by an operator after the micro-particle holding plate 13 has been mounted, the washing vessel 3 has been charged with the washing solution, and the capillaries of micro-particle array 15 have been set. By the preset function, the adherent micro-particle removing plate 11 is moved above the holders 1 holding their respective micro-particles to be first trapped, and the micro-particle trapping capillaries 8 are moved above it. The capillaries of micro-particle array 15 are individually inserted into their respective movement assist through holes 4 each to a prescribed depth. These operations are executed through the preset function by the computer 24. Therefore, the operator is required only to check that the result of the preset function is in a prescribed state.

Figure 4A:
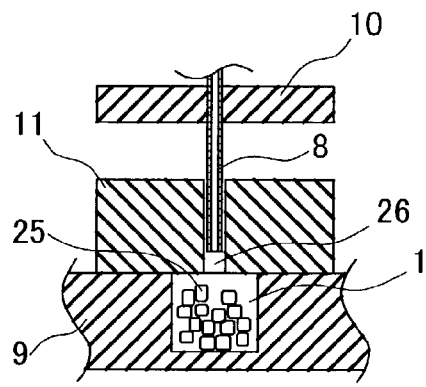
FIGS. 4(A) to 4(E) are diagrams for illustrating the sequential control of trapping of micro-particles by a micro-particle trapping capillary 8.
Figure 4D:
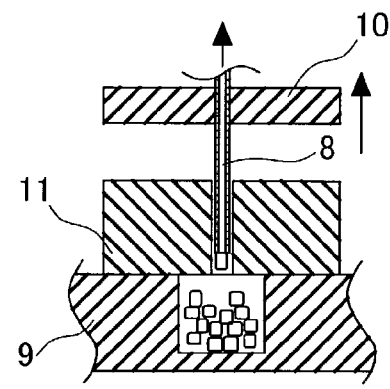
Figure 4B:
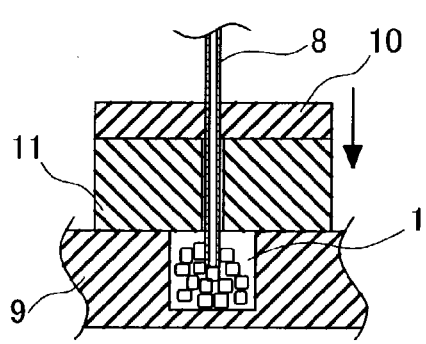

When the result of the preset function is satisfactory, the operator then performs the operation of starting the sequential operation of the computer 24. FIGS. 4(A) to 4(E), and FIGS. 5(A) to 5(D) are diagrams for illustrating the sequential control of trapping of micro-particles by the micro-particle trapping capillaries 8. FIGS. 4(A) to 4(B) are diagrams for illustrating the operation in which the trapped micro-particle are transferred to their respective capillaries of micro-particle array 15.

Figure 4E:
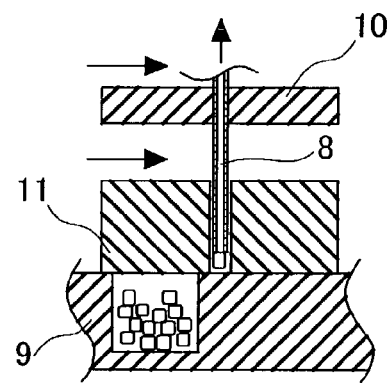
Figure 4C:
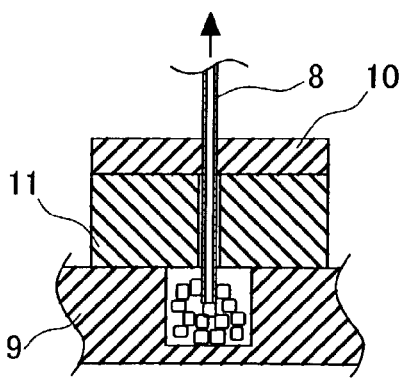

FIG. 4(A) is a diagram for showing the state in which the micro-particle trapping capillary 8 is going from the preset state shown in FIG. 3 down through the opening 26 of the adherent micro-particle removing plate 11. FIG. 4(B) is a diagram for showing the state in which the micro-particle trapping capillary 8 has gone down to the holder 1. FIG. 4(C) is a diagram for illustrating the state in which the micro-particle trapping capillary 8 is being controlled under negative pressure by the pump 16, so that a micro-particle is vacuumed onto the opening tip portion of the capillary 8, and other micro-particles also adhere to the perimeter of the opening tip portion. FIG. 4(D) is a diagram for illustrating the state in which as a result of pulling up the micro-particle trapping capillary 8 which has trapped the micro-particle at the opening tip portion, the adherent micro-particles are removed by the adherent micro-particle removing plate 11, so that only the micro-particle trapped onto the opening tip portion of the capillary 8 is being held thereon. FIG. 4(E) is a diagram for illustrating the process in which when still other micro-particles have adhered to the micro-particle trapped onto the opening tip portion of the capillary 8, and have been pulled up together, for removing them, the micro-particle trapping capillary 8 and the adherent micro-particle removing plate 11 are moved together in the direction of x axis to remove the adherent micro-particles. By this moving operation, the adherent micro-particles are removed. In addition, this moving process is temporarily stopped to pull up the micro-particle trapping capillary 8. Herein, bold arrows shown in the diagrams indicate the directions of vacuuming or pressurizing for the capillary, and the directions of movement for the movable members.

Figure 5A:
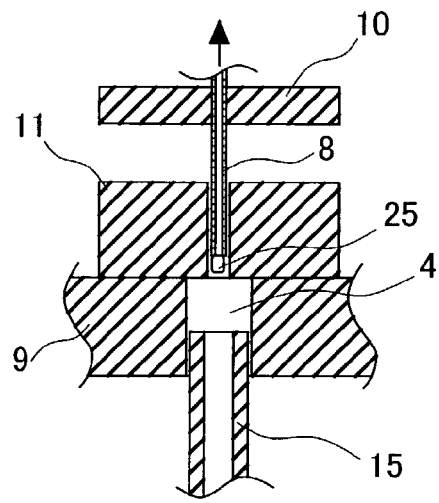
FIGS. 5(A) to 5(D) are diagrams for illustrating the operation in which the trapped micro-particle is transferred to a capillary of micro-particle array 15.
Figure 5C:
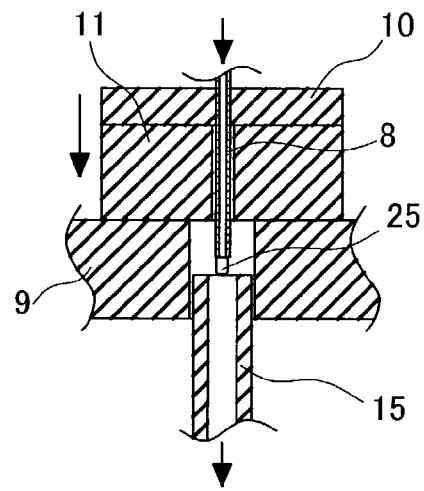
Figure 5B:
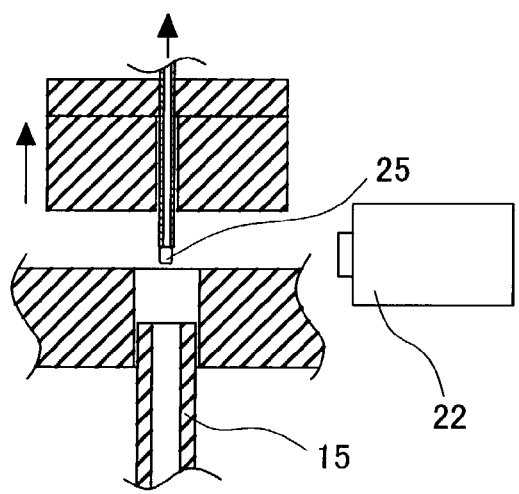
Figure 5D:
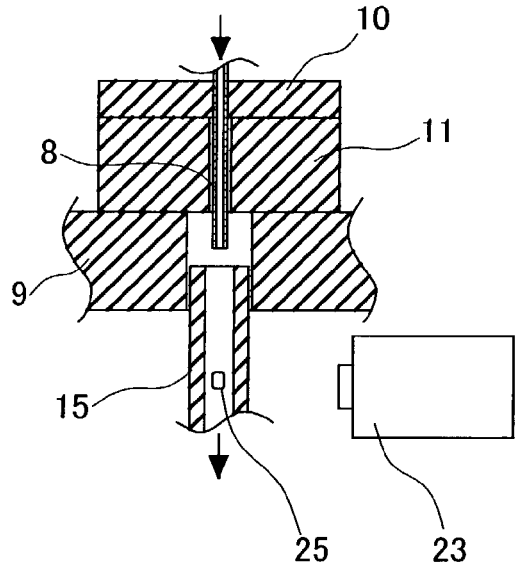

FIG. 5(A) shows the state in which the micro-particle trapping capillary 8 which has trapped the micro-particle shown in FIG. 4(E) has been moved to above the movement assist through hole 4 together with the adherent micro-particle removing plate 11. The micro-particle has been trapped onto the tip opening of the micro-particle trapping capillary 8. The capillary of micro-particle array 15 is positioned halfway in the movement assist through hole 4 at the preset stage. FIG. 5(B) shows the state in which the micro-particle trapping capillary 8 and the adherent micro-particle removing plate 11 have been moved upwards together for checking that the micro-particle is trapped onto the tip opening of the micro-particle trapping capillary 8 with reliability, which allows the vision sensor 22 to photograph the micro-particle on the tip opening of the micro-particle trapping capillary 8. When there is even one micro-particle trapping capillary 8 which has no detectable micro-particle on its tip opening at this stage, the process goes back to the preset state, and the operation of trapping of the micro-particle onto the tip opening of the micro-particle trapping capillary 8 is performed again. When the trapping operations have already completed for some of the rows of the holders 1 of the micro-particle holding plate 13, the process goes back to the immediately preceding operation. FIG. 5(C) is a diagram for illustrating the state in which the micro-particle trapping capillary 8 which has trapped the micro-particle on the tip opening has gone down into the movement assist through hole 4 to be disposed in opposing relation to the opening of the capillary of micro-particle array 15. In this state, the micro-particle trapping capillary 8 is made in pressurizing state by the pump 16, thereby to release the micro-particle trapped on the opening. FIG. 5(D) shows the state in which the released micro-particle is going down in the capillary of micro-particle array 15 set under negative pressure. This state is photographed by the vision sensor 23. When there is a capillary of micro-particle array 15 which has no detectable micro-particle for some reason, this capillary 15 is registered as a defective in the computer 24.

Upon completion of the operation in which the micro-particles are transferred to their respective capillaries of micro-particle array 15 as shown in FIGS. 4(A) to 4(E) and FIGS. 5(A) to 5(D) following the preset state, the process shifts to the operation of transferring the micro-particles in the holders 1 of the next row of the micro-particle holding plate 13 to their respective capillaries of micro-particle array 15. However, by the previous operation, the tip portion of each micro-particle trapping capillary 8 and the portion of the adherent micro-particle removing plate 11 to be in contact with the micro-particles may be contaminated by the probes of the previously trapped micro-particles, and hence a washing operation is required. This will be described by reference to FIGS. 6(A) to 6(C).

Figure 6A:
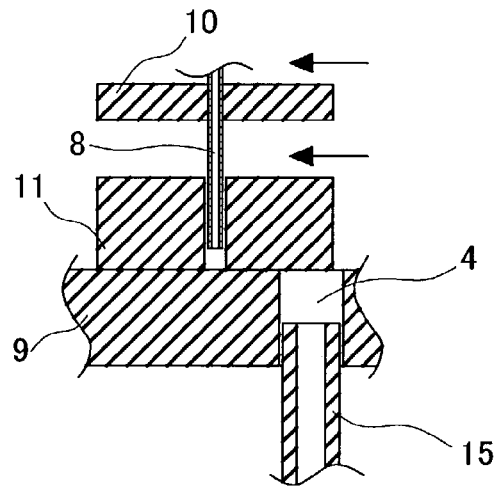
FIGS. 6(A) to 6(C) are diagrams for illustrating the operation of washing the tip portion of the micro-particle trapping capillary 8 and an adherent micro-particle removing plate 11.
Figure 6C:
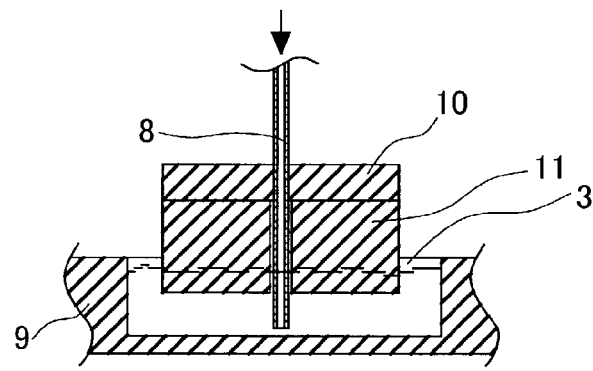
Figure 6B:
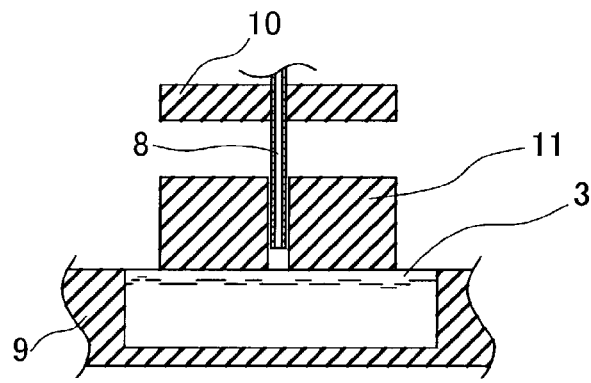

FIG. 6(A) is a diagram for showing the state in which the micro-particle trapping capillary 8 which has trapped the micro-particle shown in FIG. 5(D) is being moved in the direction of x axis together with the adherent micro-particle removing plate 11 from above the movement assist through hole 4, and going toward the washing vessel 3. FIG. 6(B) is a diagram for showing the state in which the micro-particle trapping capillary 8 has reached above the washing vessel 3 together with the adherent micro-particle removing plate 11. FIG. 6(C) is a diagram for showing the state in which the micro-particle trapping capillary 8 has been inserted in the washing vessel 3 together with the adherent micro-particle removing plate 11, so that they are being washed. In this state, the micro-particle trapping capillary 8 is so configured that its tip portion is exposed to inside the washing vessel 3.

Upon completion of the washing process, the device is set in another preset state in which the target has been shifted from the objective row in the preset state illustrated in FIG. 3 to the next row of holders 1 of the micro-particle holding plate 13. Thereafter, upon completion of the processing on this row, the same processing is also performed on the next row. Upon completion of the processings of all rows of holders 1, the capillaries of micro-particle array 15 in each of which the micro-particles are arrayed only in a number equal to the number of the holders along the x axis are fabricated only in a number equal to the number of holders 1 along the Y axis.

SECOND EXAMPLE

In Second Example, a device for micro-particle array fabrication applicable only to the case where the micro-particles 25 are held together with pure water 29 in respective holders 1 of the micro-particle holding plate 13, and the operating method thereof will be described by reference to FIGS. 7(A) to 7(F), FIGS. 8(A) to 8(C), and FIGS. 9(A) to 9(C). It is noted that like elements or elements having like functions are given like reference numerals throughout this example and First Example.

In the case where the micro-particles 25 are held in each holder 1 of the micro-particle holding plate 13 together with pure water 29, when one micro-particle is trapped by the micro-particle trapping capillary 8, micro-particles other than the micro-particle vacuumed by negative pressure onto the tip opening of the micro-particle trapping capillary 8 are removed by itself through surface tension of the pure water 29 when the tip opening of the micro-particle trapping capillary 8 is pulled out of the pure water 29. Therefore, the adherent micro-particle removing plate 11 described in First Example becomes unnecessary, and accordingly, the operational procedures are also simplified.

FIGS. 7(A) to 7(F) are diagrams corresponding to FIGS. 4(A) to 4(E).

Figure 7A:
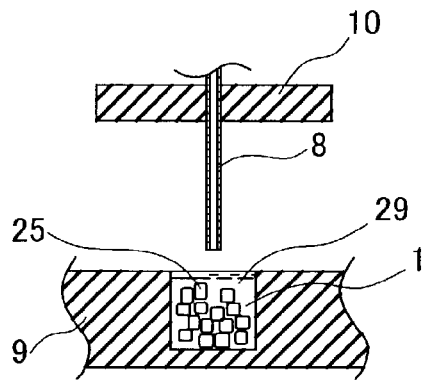
FIGS. 7(A) to 7(F) are diagrams for illustrating the sequential control of trapping of micro-particles by a micro-particle trapping capillary 8 of Second Example.
Figure 7D:
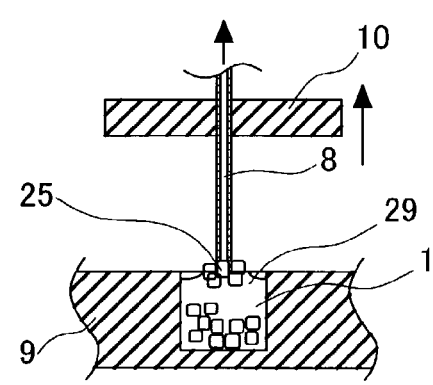
Figure 7B:
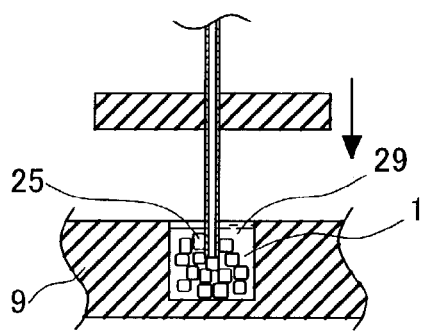
Figure 7E:
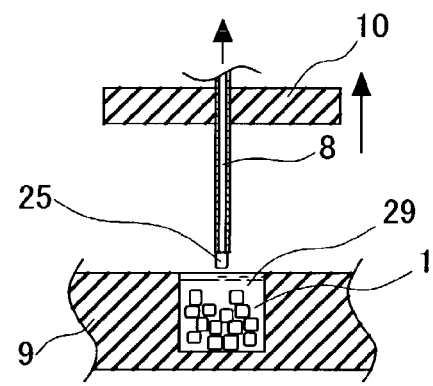
Figure 7C:
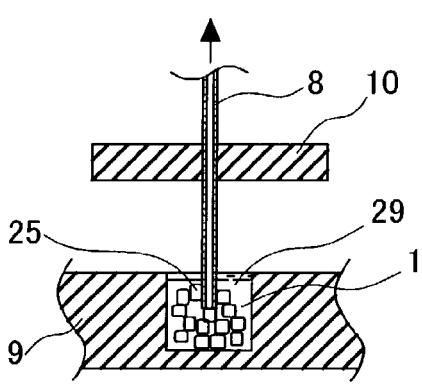
Figure 7F:
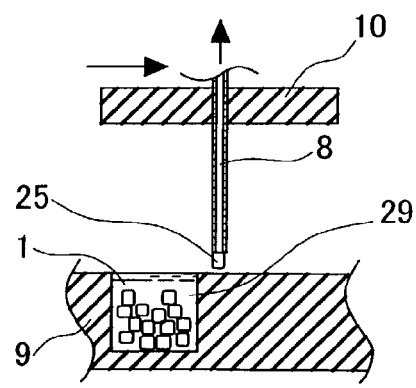

FIG. 7(A) is a diagram for showing the state in which the micro-particle trapping capillary 8 has become being preset above the holder 1 from the preset state shown in FIG. 3. In this second example, the adherent micro-particle removing plate 11 is not provided. The micro-particles 25 are present in the pure water 29 in the holder 1. FIG. 7(B) is a diagram for showing the state in which the micro-particle trapping capillary 8 has gone down into the holder 1. FIG. 7(C) is a diagram for illustrating the state in which the micro-particle trapping capillary 8 is being controlled under negative pressure by the pump 16, so that a micro-particle is vacuumed onto the opening tip portion of the capillary 8, and other micro-particles also adhere to the perimeter of the opening tip portion. FIG. 7(D) is a diagram for illustrating the state in which upon pulling up the micro-particle trapping capillary 8 which has trapped the micro-particle at the opening tip portion, the micro-particles trapped on the opening tip portion of the capillary 8 are removed by the surface tension of the pure water 29. FIG. 7(E) is a diagram for illustrating the state in which the micro-particle is consequently being pulled up while being trapped only on the opening tip portion of the capillary 8. FIG. 7(F) is a diagram for showing the state in which the micro-particle is being trapped only on the opening tip portion of the capillary 8, and pulled up, to be moved upwardly of the movement assist through hole 4. Also herein, bold arrows shown in the diagrams indicate the directions of vacuuming or pressurizing for the capillary, and the directions of movement for the movable members.

Figure 8A:
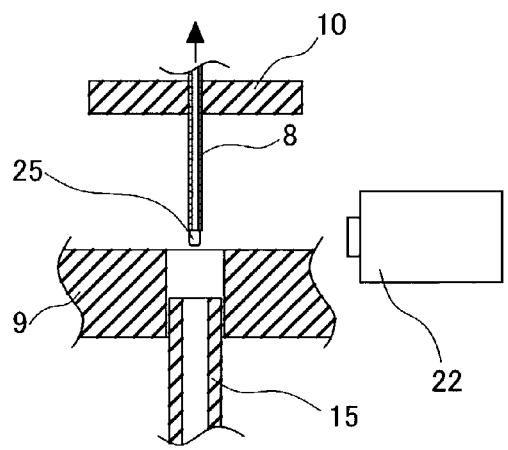
FIGS. 8(A) to 8(C) are diagrams for illustrating the operation in which the trapped micro-particle of Second Example is transferred to the capillary of micro-particle array 15.
Figure 8C:
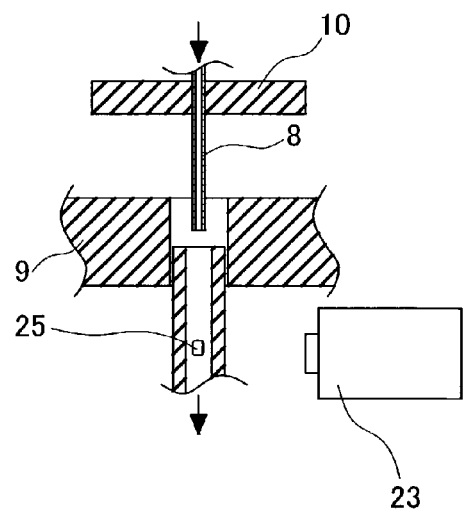
Figure 8B:
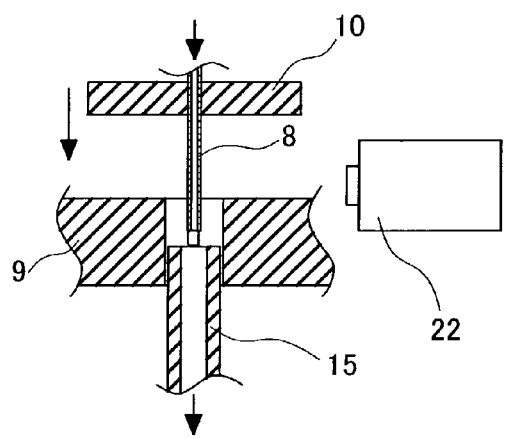

FIG. 8(A) shows the state in which the micro-particle trapping capillary 8 which has trapped the micro-particle shown in FIG. 7(F) has been moved to above the movement assist through hole 4. The micro-particle is trapped onto the tip opening of the micro-particle trapping capillary 8. The capillary of micro-particle array 15 is positioned halfway in the movement assist through hole 4 at the preset stage. In this step, the micro-particle trapping capillary 8 is moved upwardly for checking that the micro-particle is trapped onto the tip opening of the micro-particle trapping capillary 8 with reliability, which allows the vision sensor 22 to photograph the micro-particle on the tip opening of the micro-particle trapping capillary 8. When there is even one micro-particle trapping capillary 8 which has no detectable micro-particle on its tip opening, the process goes back to the preset state, and the operation of trapping of the micro-particle onto the tip opening of the micro-particle trapping capillary 8 is performed again. When the trapping operations have already been completed for some of the rows of the holders 1 of the micro-particle holding plate 13, the process goes back to the immediately preceding operation. FIG. 8(B) is a diagram for illustrating the state in which the micro-particle trapping capillary 8 which has trapped the micro-particle on the tip opening has gone down into the movement assist through hole 4 to be disposed in opposing relation to the opening of the capillary of micro-particle array 15. In this state, the micro-particle trapping capillary 8 is made in pressurizing state by the pump 16, thereby to release the micro-particle trapped on the opening. FIG. 8(C) shows the state in which the released micro-particle is going down in the capillary of micro-particle array 15 set under negative pressure. This state is photographed by the vision sensor 23. When there is a capillary of micro-particle array 15 which has no detectable micro-particle for some reason, this capillary 15 is registered as a defective in the computer 24.

Figure 9A:
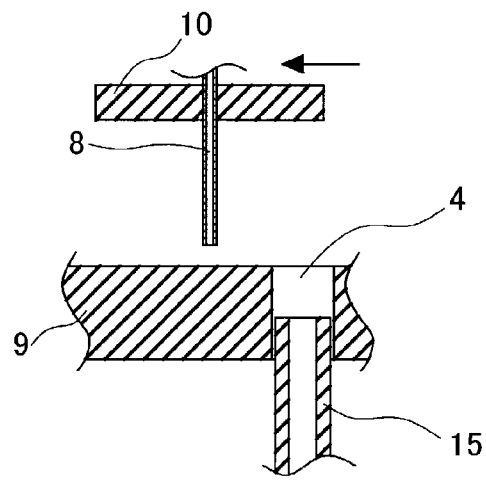
FIGS. 9(A) to 9(C) are diagrams for illustrating the operation of washing the tip portion of the micro-particle trapping capillary 8 and the adherent micro-particle removing plate 11 of Second Example.
Figure 9C:
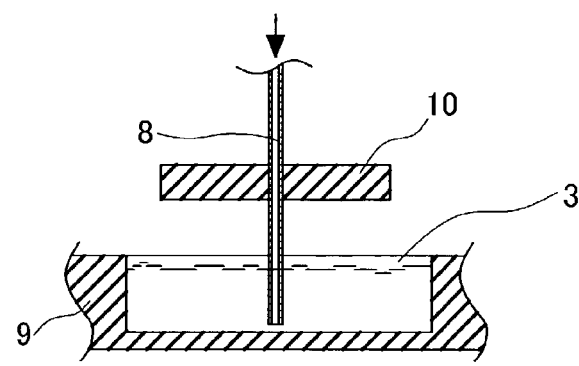
Figure 9B:
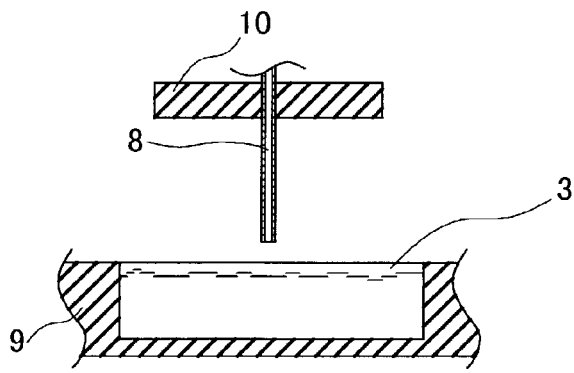

FIG. 9(A) is a diagram for showing the state in which the micro-particle trapping capillary 8 which has trapped the micro-particle shown in FIG. 8(C) is being moved in the direction of x axis from above the movement assist through hole 4, and going toward the washing vessel 3. FIG. 9(B) is a diagram for showing the state in which the micro-particle trapping capillary 8 has reached above the washing vessel 3. FIG. 9(C) is a diagram for showing the state in which the micro-particle trapping capillary 8 has been inserted in the washing vessel 3, so that it is being washed. In this state, the micro-particle trapping capillary 8 is so configured that its tip portion is exposed to inside the washing vessel 3.

Upon completion of the washing process, also in Second Example, the device is set in another preset state in which the target has been shifted from the objective row in the preset state illustrated by reference to FIG. 2 to the next row of holders 1 of the micro-particle holding plate 13. Thereafter, upon completion of the processing on this row, the same processing is also performed on the next row. Upon completion of the processings of all rows of holders 1, the capillaries of micro-particle array 15 in each of which the micro-particles are arrayed in a number equal to the number of the holders 1 along the x axis are fabricated in a number equal to the number of the holders 1 along the Y axis.

Figure 10:
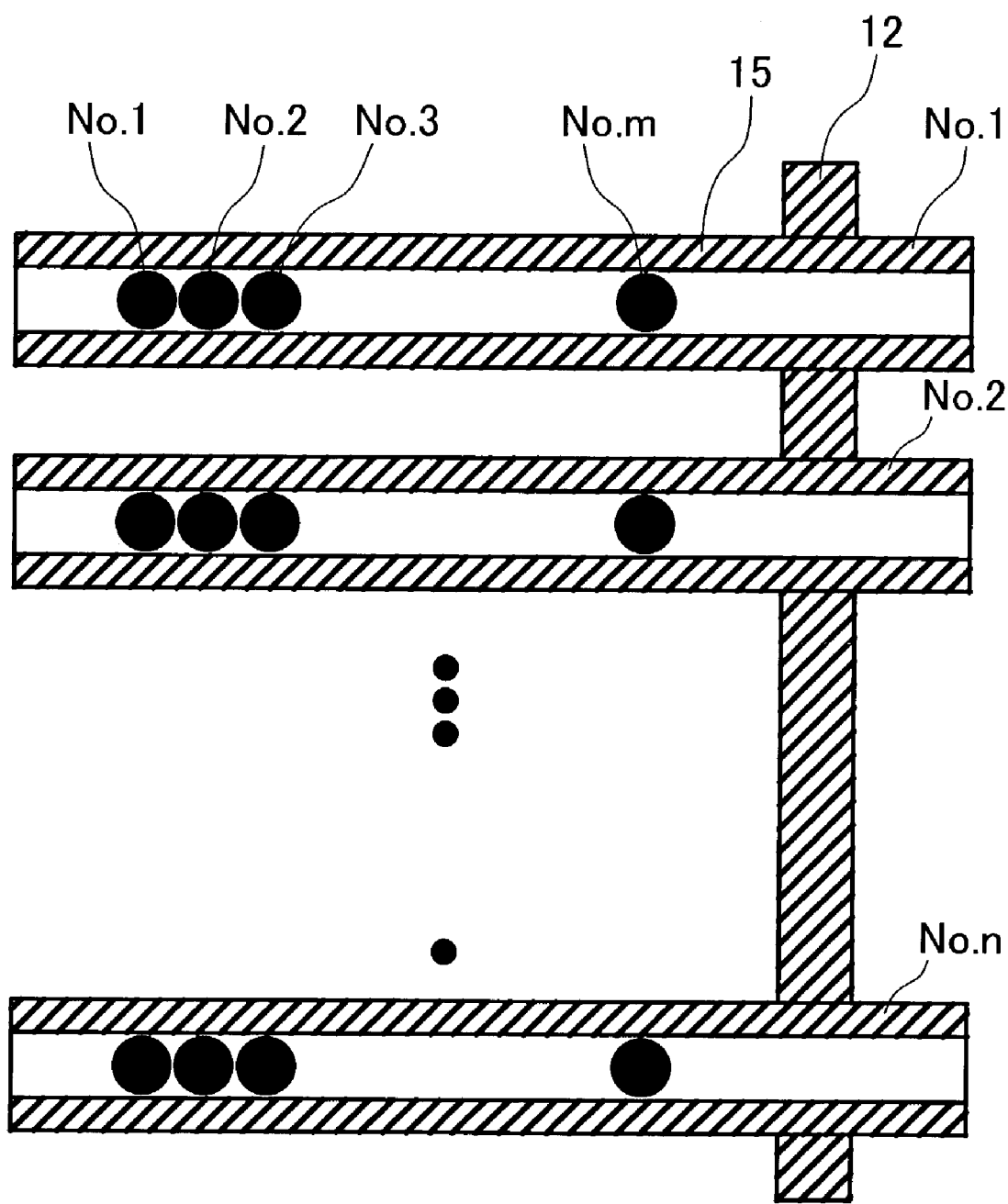
FIG. 10 is a diagram for showing an example of the completed form of the capillaries of micro-particle array 15 obtained in First Example and Second Example.

FIG. 10 is a cross sectional view for schematically showing the example of a plurality of capillaries of micro-particle array 15 obtained by the one having m×n holders in accordance with Example 1 or 2. The capillaries 15 can be provided in this state as a capillary set. Alternatively, they are released from the holder 12, and provided as capillaries of micro-particle array on a one-by-one basis. Of course, at this stage, in order to prevent the micro-particles introduced in each capillary from overflowing, and to keep the orderly arrayed state, hollow small tubes each having an outer diameter equal to the capillary inner diameter are inserted into the opposite ends to prevent the micro-particles from moving, but not shown. This is because a sample is required to be introduced into the capillary of micro-particle array.

THIRD EXAMPLE

Figure 11A:
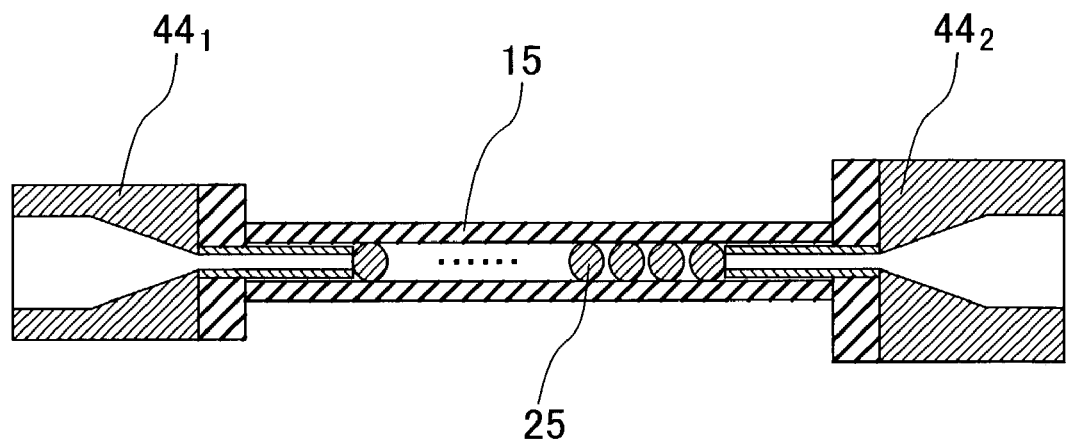
FIGS. 11(A) and 11(B) are diagrams each for showing an example of one micro-particle array in the commercially available form devised for convenience of a user.
Figure 11B:
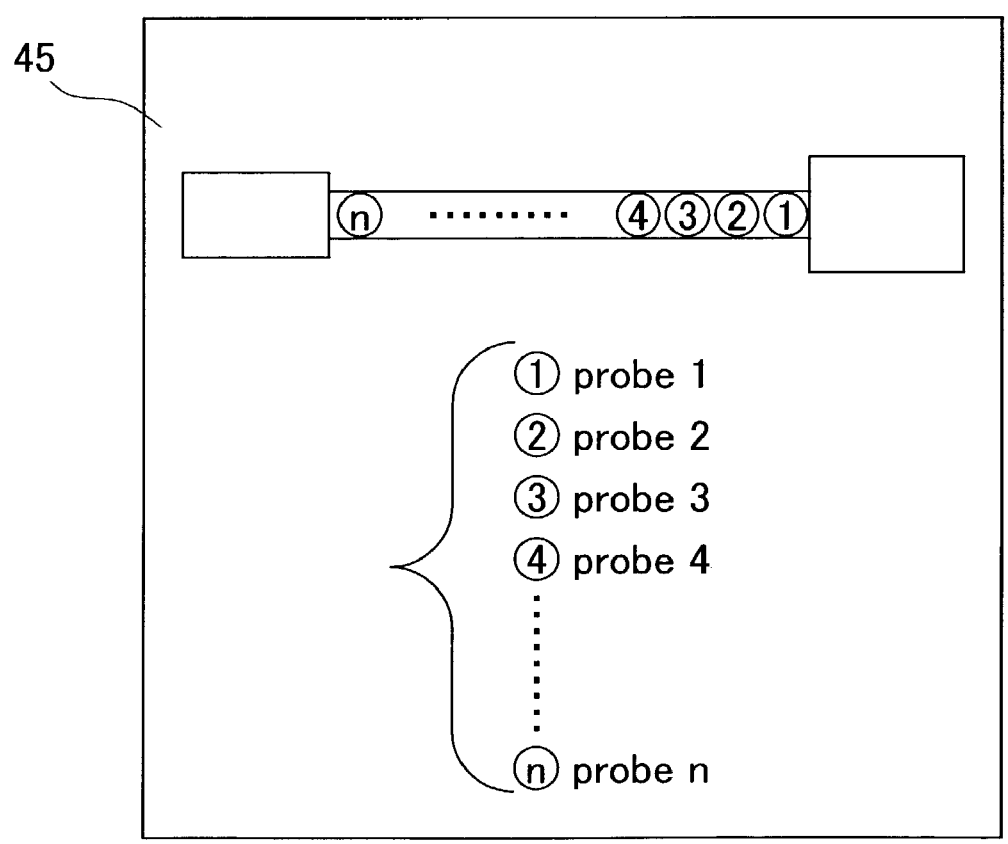

This third example relates to one example of the micro-particle array fabricated by using the device for micro-particle array fabrication of the present invention of FIG. 1 in commercially available form as a low-cost tool for genetic examination. In FIG. 10, the array is shown in the form of a capillary group. Whereas, as shown in FIGS. 11(A) and 11(B), the array is shown in such a commercially available form of one micro-particle array that the opposite ends of the capillary of micro-particle array 15 are configured each in the form devised for convenience of a user. As shown in FIG. 11(A), connectors 44$_1$ and 44$_2$ made of glass, through each of which a capillary having an outer diameter as large as the inner diameter of the capillary of micro-particle array 15, and having an inner diameter smaller than the outer diameter of the probe-immobilized micro-particle can be inserted into the capillary of micro-particle array 15 to approximately several millimeters and attached thereto, are added to the opposite ends. The other end of each of the connectors 44$_1$ and 44$_2$ is in tapered form, so that a polyimide-coated glass capillary for pouring a sample solution can be attached thereto. This micro-particle array is sold with micro-particle array ID 45 indicating the kinds of the probes included therein and the arraying order as shown in FIG. 11(B), resulting in a tool convenient for a user to use. Further, as shown in FIG. 11(A), by causing a difference in size between the connectors 44$_1$ and 44$_2$ at opposite ends, it is possible to clearly demonstrate the front-to-back arraying order.

FOURTH EXAMPLE

Figure 12A:
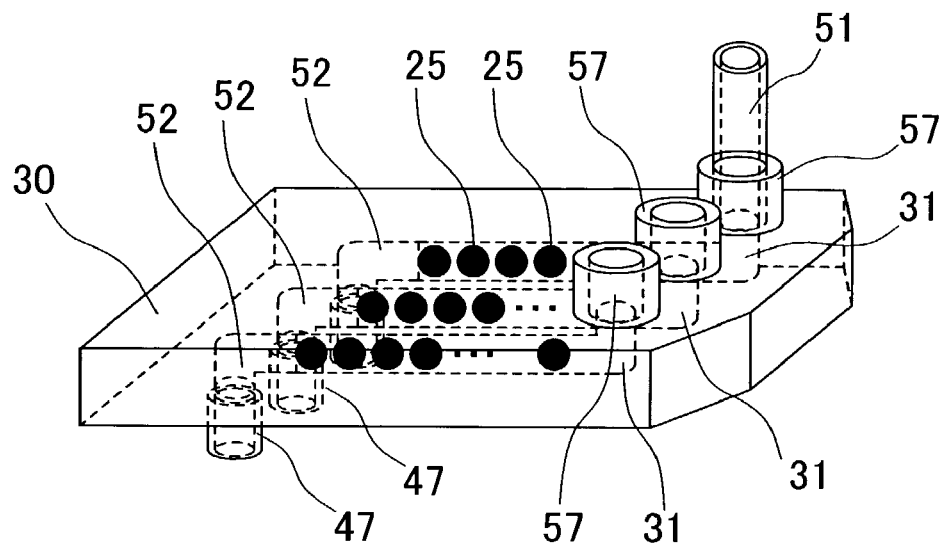
FIGS. 12(A) and 12(B) are diagrams each for showing an example of the micro-particle array in such a form that channels each having an inlet and an outlet are formed in a chip.
Figure 12B:
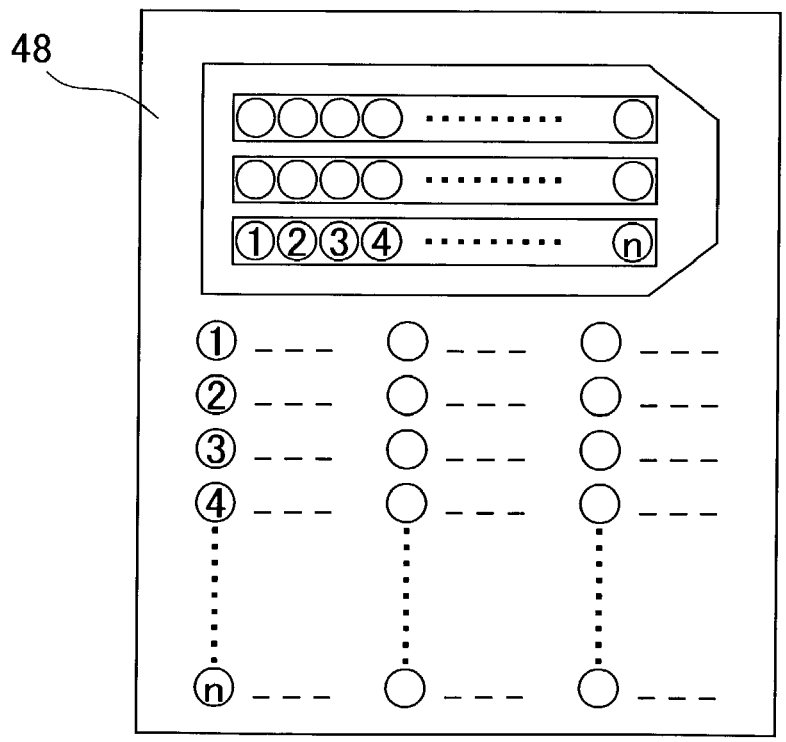

FIGS. 12(A) and 12(B) are diagrams for showing an example of a micro-particle array in such a form that capillaries are formed in a chip provided with channels each having an inlet and an outlet. In First Example or Second Example, the capillaries of micro-particle array are formed in such a manner that only required number of independent capillaries are configured in a bundle. Whereas, in Fourth Example, as shown in FIG. 12(A), a chip for micro-particle array 30 is provided. In this chip, a group of capillaries of micro-particle array as shown in FIG. 10 is configured. One end of each capillary opens through the top face of the chip 30 as a micro-particle inlet 31. The other end of each capillary opens through the bottom face of the chip 30 as an outlet 52. Herein, the edge on the other end side of the capillary is provided with a bump to have an inner diameter smaller than the outer diameter of the micro-particle 25. A reference numeral 57 denotes a connector, which is disposed coaxially with the micro-particle inlet 31 opening through the top face of the chip 30 about a common central axis. The inner diameter thereof is large enough to be capable of receiving the capillary 51 for coordination with the movement assist through hole 4 described by reference to FIG. 1. Herein, as a matter of course, the inner diameter of the capillary 51 is larger than the outer diameter of the micro-particle 25 to be fed therein via the movement assist through hole 4, and it is desirably the same as that of the capillary 51 of FIG. 1. For simplification of the drawing, only one capillary 51 is shown. However, it is needless to say that the capillaries 51 can be provided in a number equal to the number of the capillaries of micro-particle array of the capillary group in the chip. Further, the capillary 51 is required to have a length such that the micro-particle to be introduced can be photographed by the vision sensor 23 when the chip for micro-particle array 30 is held and set in the holding portion of the actuator 50 as with the holder 12. The outlet 52 on the other end of the capillary is provided with a connector 47 corresponding to the socket 27 of FIG. 1 for evacuation. Any appropriate inner diameter of the connector 47 is acceptable so long as the outlet 52 on the other end of the capillary has an inner diameter capable of inhibiting the movement of the micro-particle 25.

FIG. 12(B) is a plan view for showing an embodiment of the micro-particle array chip 30 when seen as a product. In this state, the connector 57 and the capillary 51 have been removed. Further, although not indicated from the diagram, the micro-particle inlet 31 portion is closed. This micro-particle array chip 30 is sold with micro-particle array ID 45 indicating the kinds of the probes included in the micro-particle array chip 30, and the arraying order, resulting in a tool convenient for a user to use. Further, by causing a difference in shape between the opposite ends of the micro-particle array chip 30, it is possible to consider the front-to-back arraying order.

FIFTH EXAMPLE

Figure 13:
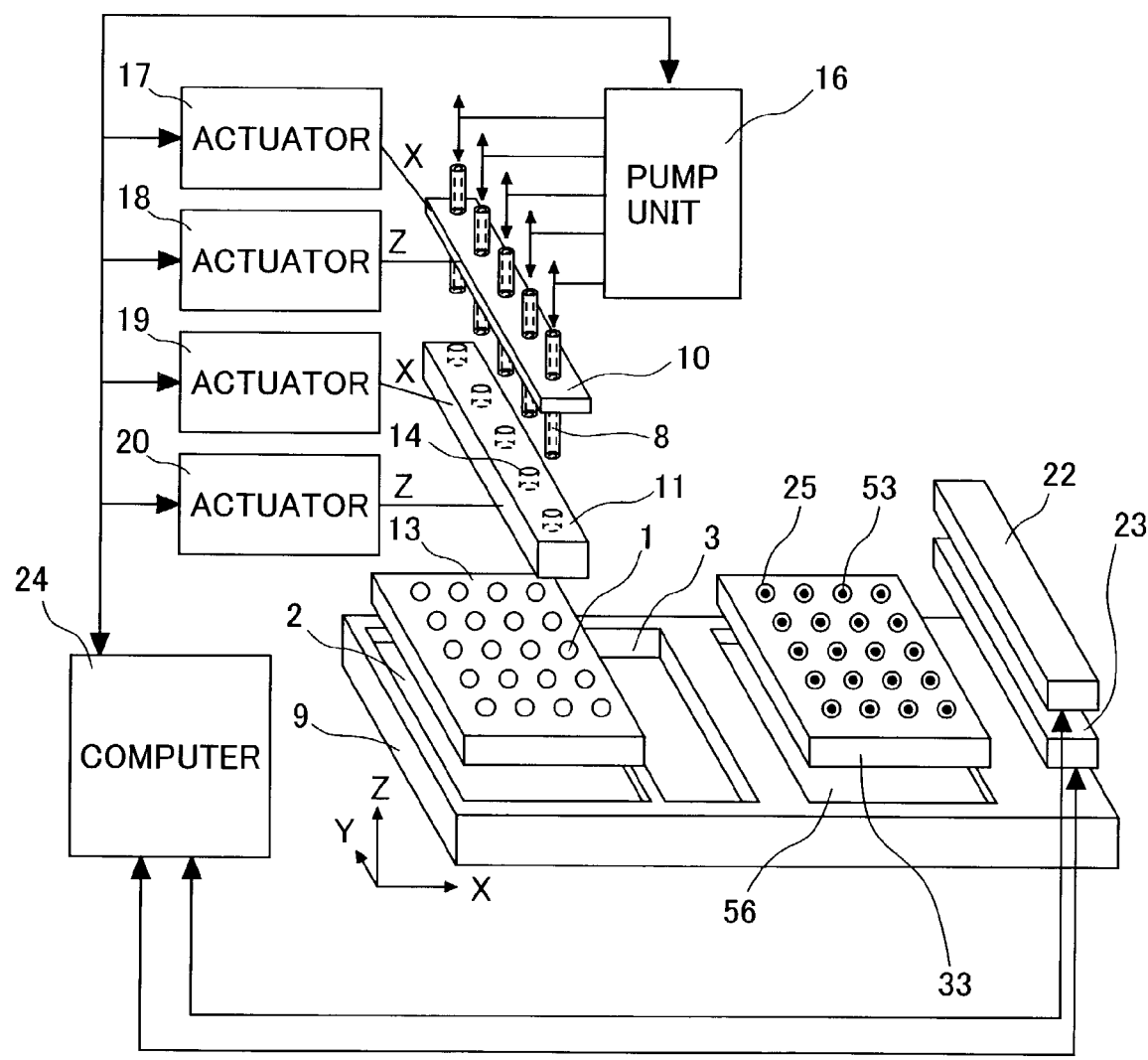
FIG. 13 is a diagram for showing an example of a device for fabricating a planar micro-particle array in place of the capillaries of micro-particle array 15.

Fifth Example proposes a device for fabricating a planar micro-particle array in place of the capillaries of micro-particle array 15. An example of the whole device configuration is shown in FIG. 13. Like elements having like functions are given like reference numerals throughout First Example shown in FIG. 1 and this example. As indicated from the comparison with FIG. 1, the device is so configured that a planar micro-particle array 33 is disposed on top of the base 9. The movement assist through hole 4 is not required to be disposed. A reference numeral 56 denotes a concave portion for positioning, which is disposed so that the micro-particle array 33 can assume a precise position with respect to the base 9 as with the plate mounting site 2 in the example of FIG. 1. In this example, every time when micro-particles have been trapped by the micro-particle trapping capillaries 8, they are positioned in their respective holders 53 of the micro-particle array 33 in a prescribed order. In this step, as a matter of course, the micro-particles are monitored by the vision sensor 22 for confirmation. After the micro-particles have been transferred into their respective holders 53, the micro-particle trapping capillaries 8 are inserted in the washing vessel 33 to be washed in the same manner as in First Example. Then, the operation of trapping the next micro-particles is repeated. The micro-particles positioned in a prescribed order in their respective holders 53 of the micro-particle array 33 are monitored by the vision sensor 23, so that the array of micro-particle is confirmed. This can also be covered by the vision sensor 22.

In Fifth Example, the vacuuming operation of the capillary of micro-particle array is not required, which allows simplification of the device.

(Application example of the capillary of micro-particle array, or the like in accordance with the present invention)

Herein, a description will be given to the use example in which by the capillary 15 of array of micro-particles having DNA probes attached thereto in a given order fabricated by the example of the device for micro-particle fabrication of the present invention of FIG. 1, a specific fluorescence-labeled target DNAs are hybridized on the DNA probe array by reference to FIGS. 14(A) and 14(B).

Figure 14A:
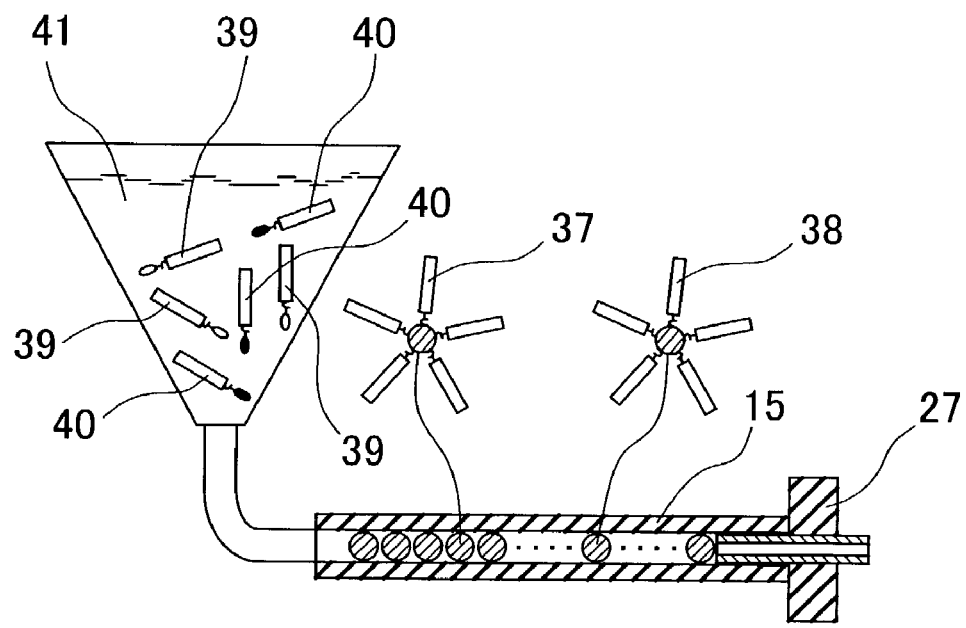
FIGS. 14(A) and 14(B) are diagrams each for showing a use example of a capillary of micro-particle array 15 with DNA probes in a given order fabricated by the example of the device for micro-particle array fabrication of FIG. 1.
Figure 14B:
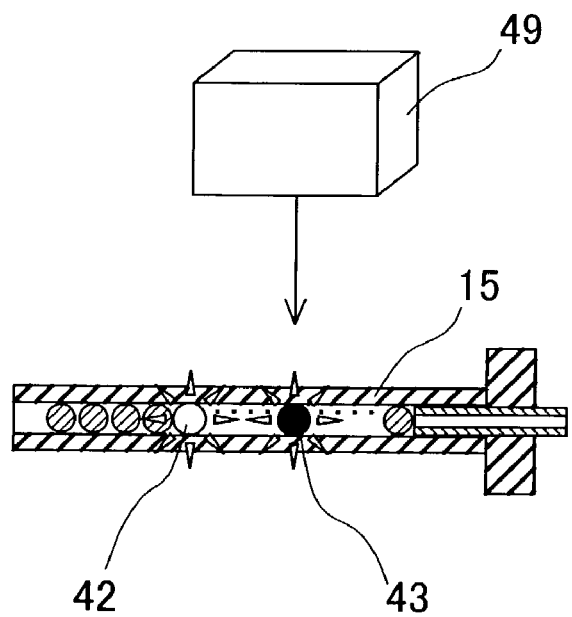

In FIGS. 14(A) and 14(B), the capillary of micro-particle array 15 includes therein a micro-particle having single stranded DNA probes 37 each having Sequence 1 immobilized thereto, and another micro-particle having single stranded DNA probes 38 each having Sequence 2 immobilized thereto out of 24 kinds of probe DNAs of 24 kinds of 18-base synthetic oligonucleotides modified with a thiol group at 5' terminal and having different base sequences. Into this capillary 15, a sample containing single stranded target DNAs 39 each having a Cy3 labeled Sequence 3 complementary to Sequence 1, and Texas Red labeled single stranded target DNAs 40 each having Sequence 4 complementary to Sequence 2 was poured. Thus, it was verified whether or not the target DNAs would bind to their respective corresponding probe DNAs as intended.

```
(Sequence 1)
5'-thiol-ATCTGACTGCGGCTCCTC-3'

(Sequence 2)
5'-thiol-CTACCTGCTCCCTGGACG)-3'

(Sequence 3)
5'-Cy3-GAGGAGCCGCAGTCAGAT)-3'

(Sequence 4)
5'-Texas Red-CGTCCAGGGAGCAGGTAG)-3'
```

A 20 mM phosphate buffer (pH 7.0) solution 41 containing the single stranded target DNAs 39 and the single stranded target DNAs 40 each in a concentration of 1 µM is poured into the capillary 15 of micro-particle array 15 in which the DNA probe array has been fabricated as shown in FIG. 14(A), thereby to effect hybridize at 45° C. The solution is fed into the capillary by using a syringe pump, or the like. After the reaction, the residual target DNAs which has not contributed to the hybridization are successively washed with the 20 mM phosphate buffer (pH 7.0) solution 41 and pure water, and dried. Thereafter, by using a mercury lamp as a light source, a long pass filter for Cy3 and a long pass filter for Texas Red centered at the emission wavelengths of Cy3 and Texas Red, respectively, are successively used to perform observation of the respective micro-particles in the capillary of micro-particle array 15 by means of a fluorescence microscope 49. As shown in FIG. 14(B), out of the arrayed micro-particles 25, a prescribed micro-particle emits fluorescence 42 of Cy3, and further, another prescribed micro-particle emits fluorescence 43 of Texas Red. This indicates that the single stranded target DNA 40 and the single stranded target DNA 41 have been surely hybridized to the single stranded DNA probe 38 and the single stranded DNA probe 39, respectively. It has been shown that it was possible to fabricate a DNA probe array in the capillary of micro-particle array 15 in a given order without affecting the probes by means of this arraying device.

Below, embodiments of the present invention will be listed concisely in a summarized manner.

1. A method for micro-particle array fabrication, comprising: (1) a step of allowing a plurality of micro-particles having different kinds of probes, which will bind to biomaterials, immobilized thereto, and having roughly the same outer diameter, to be held in a plurality of different holders one-dimensionally or two-dimensionally arrayed according to the kinds of the probes, vacuuming the plurality of the micro-particles in the holders from one end of a first capillary having an inner diameter not allowing passage of only one of the micro-particles therethrough, and holding only one of the micro-particles on the other end of the first capillary; (2) a step of moving the other end of the first capillary to a position opposed to one end of the opening of a second capillary or a chip provided with a channel having an inlet and an outlet, having an inner diameter allowing passage of only one of the micro-particles therethrough; and (3) a step of pressurizing the micro-particle held on the other end of the first capillary from the one end of the first capillary, and vacuuming the micro-particle through a vacuum port smaller than the outer diameter of the micro-particle from the other end of the opening of the second capillary or the chip, thereby allowing the micro-particle to be held inside the second capillary or the chip, wherein the micro-particles are held inside the second capillary or the chip, such that the micro-particles having different kinds of probes immobilized thereto are arrayed in a prescribed order inside the second capillary or the chip.

2. The method for micro-particle array fabrication according to the item (1), further comprising a step of detecting whether or not the micro-particle has been held on the other end of the first capillary.

3. The method for micro-particle array fabrication according to the item (1), further comprising a step of detecting whether or not the micro-particle has been held inside the second capillary or the chip.

4. The method for micro-particle array fabrication according to the item (1), further comprising a step of storing the kinds of the probes immobilized to the micro-particles held inside the second capillary or the chip in a storage medium.

5. A method for micro-particle array fabrication, comprising: (1) a step of allowing a plurality of micro-particles having different kinds of probes, which will bind to biomaterials, immobilized thereto, and having roughly the same outer diameter, to be held in a plurality of holders disposed at a prescribed row-to-row spacing according to the kinds of the probes on a row-by-row basis, vacuuming the plurality of the micro-particles in the holders from one ends of a plurality of first capillaries each having an inner diameter not allowing passage of only one of the micro-particles therethrough, and having one ends arrayed in a row at the prescribed spacing, and allowing only one of the micro-particles to be held on each of the other ends of the plurality of the first capillaries; (2) a step of moving each of the other ends of the plurality of the first capillaries to a position opposed to one end of each opening of a plurality of second capillaries or channels of a chip each having an inlet and an outlet, of which one ends are arrayed in a row at the prescribed spacing, and each of which has an inner diameter allowing passage of only one of the micro-particles; and (3) a step of pressurizing the micro-particles held on the other ends of the plurality of the first capillaries from the respective one ends of the plurality of the first capillaries, and vacuuming the micro-particles through vacuum ports each smaller than the outer diameter of the micro-particle from the other ends of the openings of the plurality of the second capillaries or the channels of the chip, thereby to allow the micro-particles to be held inside the plurality of the second capillaries or the plurality of the channels in the chip, wherein the micro-particles are held inside the plurality of the respective second capillaries or the plurality of the respective channels of the chip at the same time, such that the micro-particles having different kinds of the probes respectively immobilized thereto are arrayed in a prescribed order inside the plurality of the respective second capillaries or the respective channels of the chip.

6. The method for micro-particle array fabrication according to the item (5), further comprising a step of detecting whether or not the micro-particles have been held on their respective other ends of the plurality of the first capillaries.

7. The method for micro-particle array fabrication according to the item (5), further comprising a step of detecting whether or not the micro-particles have been held inside the plurality of the respective second capillaries or the respective channels in the chip.

8. The method for micro-particle array fabrication according to the item (5), further comprising a step of storing the kinds of the probes respectively immobilized to the micro-particles held inside the plurality of the respective second capillaries or the respective channels in the chip in a storage medium.

9. A method for selling a micro-particle array, comprising selling a micro-particle array in which micro-particles having different kinds of probes, which will bind to biomaterials, immobilized to their respective micro-particles, and roughly the same outer diameter are arrayed inside a capillary or a chip provided with a channel having an inlet and an outlet, having an inner diameter allowing passage of only one of the micro-particles, together with a storage medium storing the kinds of the probes immobilized to the micro-particles as a pair with the arraying order of the micro-particles.

10. A method for carrying a micro-particle having biomaterial probes immobilized thereto, comprising: (1) a step of allowing a plurality of micro-particles having different kinds of probes, which will bind to biomaterials, immobilized thereto, and having roughly the same outer diameter, to be held in a plurality of first holders disposed at a prescribed row-to-row spacing according to the kinds of the probes, vacuuming the micro-particles from one ends of a plurality of capillaries each having an inner diameter not allowing passage of only one of the micro-particles therethrough, and having one ends arrayed in a row at the prescribed spacing, and allowing only one of the micro-particles to be held on each of the respective other ends of the plurality of the capillaries; (2) a step of moving each of the other ends of the capillaries to above the respective openings of a plurality of second holders arrayed at a spacing corresponding to the prescribed spacing between the first holders; and (3) a step of pressurizing the micro-particles respectively held on the other ends of the plurality of the capillaries from the respective one ends of the plurality of the capillaries, and dropping the plurality of the micro-particles into the second holders, wherein given ones of the micro-particles are introduced one by one into each of the plurality of the second holders.

11. A device for carrying a micro-particle having biomaterial probes immobilized thereto, comprising: a plurality of first holders disposed at a prescribed row-to-row spacing, for holding therein a plurality of micro-particles having different kinds of probes, which will bind to biomaterials, immobilized thereto, and having roughly the same outer diameter, according to the kinds; a plurality of capillaries each having an inner diameter not allowing passage of only one of the micro-particles therethrough, and having their one ends arrayed in a row at the prescribed spacing; a vacuuming means for vacuuming the micro-particles from the one ends of the plurality of the capillaries, and allowing only one of the micro-particles to be held on each of the respective other ends of the plurality of the capillaries; a plurality of second holders of which one ends are arrayed at a spacing corresponding to the prescribed spacing between the first holders; a means for moving each of the other ends of the capillaries to above the respective openings of the plurality of the second holders; and a means for pressurizing the micro-particles respectively held on the other ends of the plurality of the capillaries from the respective one ends of the plurality of the capillaries, wherein given ones of the micro-particles are introduced one by one into each of the plurality of the second holders.

As described above, in accordance with the present invention, it is possible to fabricate a micro-particle array targeted for a biomaterial such as DNA or protein in a capillary or a chip provided with a channel at a low manufacturing cost with efficiency. Further, it becomes possible to sell the micro-particle array fabricated in accordance with the present invention as a low-cost chip for genetic examination.

What is claimed is:

1. A device for micro-particle array fabrication, comprising:
- a container having one-dimensionally or two-dimensionally arrayed different individual holders, the holders holding therein a plurality of micro-particles having different kinds of probes, which will bind to biomaterials, immobilized thereto and having roughly the same outer diameter, according to the kinds of the probes;
- at least one capillary having an inner diameter, which prevents passage of any one of the micro-particles therethrough, having an opening at one end, the opening accommodating thereon only one of the micro particles;
- a first pressure applying means applying a negative pressure or a positive pressure to the capillary;
- a vessel for receiving the micro-particles and forming a micro-particle group;
- a moving means moving the opening of the capillary holding the micro-particle to a prescribed position of the vessel;
- a computer for controlling the movement and the position of the capillary, and the pressure to be applied to the capillary; and
- a second pressure applying means applying a negative pressure to the vessel when the first pressure applying means applies the positive pressure to the capillary.

2. The device for micro-particle array fabrication according to claim 1, further comprising a detecting means detecting whether or not said one of the micro-particles is being held on the opening at one end of the capillary controlled under negative pressure, wherein when it is not possible to confirm the micro-particle being held thereon, the computer repeats the computer repeats the operation of allowing the micro-particle to be held on the opening at one end of the capillary controlled under negative pressure.

3. The device for micro-particle array fabrication according to claim 1, further comprising a detecting means detecting an existence of the micro-particle in the vessel, after the state in which said one of the micro-particles held on the opening at one end of the capillary controlled under the negative pressure is detected, the micro-particle is moved to a prescribed position in the vessel, and the capillary has been switched from under the negative pressure to under the positive pressure.

4. The device for micro-particle array fabrication according to claim 1, wherein the vessel including the micro-particles is to be provided to a user together with information on the kinds of the probes immobilized to respective micro-particles.

5. The device for micro-particle array fabrication according to claim 1, wherein the holder is set for holding liquid which contains the micro-particles, and the opening contacts with the micro-particles in the liquid to hold said one of the micro-particles outside of the holder.

6. The device for micro-particle array fabrication according to claim 1, further comprising a plate having at least one hole, the hole is set to correspond to the capillary, wherein the capillary moves through said hole when the first pressure applying means applies the negative pressure to the capillary.

7. The device for micro-particle array fabrication according to claim 6, wherein $OD \leq OD' < 2R$ is satisfied, wherein OD is an outer diameter of the capillary, OD' is a diameter of the hole, and R is an outer diameter of the micro-particles.

8. A device for micro-particle array fabrication, comprising:
- a container having two-dimensionally arrayed different individual holders, the holders set for holding therein a plurality of micro-particles having different kinds of probes, which will bind to biomaterials, immobilized thereto, and having roughly the same outer diameter, according to the kinds of the probes;
- a plurality of capillaries whose number equals to a number of rows of the two-dimensionally arrayed holders, arrayed at a spacing substantially equal to the spacing between the rows, the capillaries each having an inner diameter, which prevents passage of any one of the micro-particles therethrough, each having an opening at one end, the openings being inserted into respective two-dimensionally arrayed holders on a row-by-row basis, and each of the openings holding only one of the micro-particles thereon;
- a first applying pressure means applying a negative pressure or a positive pressure to the capillary;
- a vessel for receiving the micro-particles in a prescribed order on a row-by-row basis, and forming a micro-particle group;
- a moving means moving the openings of the capillaries each holding the micro-particle to their respective prescribed positions of the vessel;
- a computer for controlling the movement and the position of the capillaries, and the pressures to be applied to the capillaries; and
- a second pressure applying means applying a negative pressure to the vessel when the first pressure applying means applies the positive pressure to the capillary.

9. The device for micro-particle array fabrication according to claim 8, further comprising a detecting means detecting whether or not said one of the micro-particles is being held on the opening at one end of each of the plurality of the capillaries controlled under negative pressure, wherein when it is not possible to confirm the micro-particle being held for even one of the capillaries, the computer repeats the operation of allowing the micro-particle to be on the opening at one end of each of the plurality of the capillaries controlled under negative pressure.

10. The device for micro-particle array fabrication according to claim 8, further comprising a detecting means detecting an existence of the micro-particle in the vessel, after the state in which said one of the micro-particles held on the opening at one end of each of the plurality of the capillaries controlled under the negative pressure is detected, the micro-particle is moved to a prescribed position in the vessel, and the plurality of the capillaries is switched from under the negative pressure to under the positive pressure.

11. The device for micro-particle array fabrication according to claim 8, wherein the vessel including the micro-particles is to be provided to a user together with information on the kinds of the probes immobilized to respective micro-particles.

* * * * *

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Template DNA originating from synthesized
      oligonucleotide

<400> SEQUENCE: 1
atctgactgc ggctcctc                                                    18

<210> SEQ ID NO 2

-continued

```
<211> LENGTH: 18
<212> TYPE: DNA
<213> ORGANISM: Artificial Sequence
<220> FEATURE:
<223> OTHER INFORMATION: Template DNA originating from synthesized
      oligonucleotide

<400> SEQUENCE: 2
ctacctgctc cctggacg                                                18

<210> SEQ ID NO 3
<211> LENGTH: 18
<212> TYPE: DNA
<213> ORGANISM: Artificial Sequence
<220> FEATURE:
<223> OTHER INFORMATION: Template DNA originating from synthesized
      oligonucleotide

<400> SEQUENCE: 3
gaggagccgc agtcagat                                                18

<210> SEQ ID NO 4
<211> LENGTH: 18
<212> TYPE: DNA
<213> ORGANISM: Artificial Sequence
<220> FEATURE:
<223> OTHER INFORMATION: Template DNA originating from synthesized
      oligonucleotide

<400> SEQUENCE: 4
cgtccaggga gcaggtag                                                18
```